United States Patent [19]

Baron et al.

[11] Patent Number: 4,874,803

[45] Date of Patent: Oct. 17, 1989

[54] DIANHYDRIDE COUPLED POLYMER STABILIZERS

[75] Inventors: Arthur L. Baron, Getzville; Terry N. Myers, Williamsville; Jerome Wicher, West Seneca, all of N.Y.

[73] Assignee: Pennwalt Corporation, Philadelphia, Pa.

[21] Appl. No.: 99,192

[22] Filed: Sep. 21, 1987

[51] Int. Cl.[4] .......................... C08K 3/34; C08K 5/47; C07D 403/10; C07D 487/06

[52] U.S. Cl. ............................ 524/94; 524/91; 524/98; 524/100; 524/103; 524/105; 524/191; 524/193; 524/195; 546/36; 546/77; 546/78; 546/110; 546/142; 548/261; 548/348; 548/423; 548/433; 548/465; 548/466; 548/475; 548/483; 558/154; 560/34; 560/86; 562/432; 562/439; 562/503; 562/505; 562/509; 562/511; 562/556; 562/560; 556/407; 556/419; 556/421; 564/15; 564/148; 564/149; 564/151

[58] Field of Search ............... 548/433, 423, 475, 465, 548/348, 483, 261, 466, 126; 546/36, 77, 78, 110, 142; 560/34, 86; 524/98, 105, 191, 192, 193, 194, 100, 103, 91; 564/148, 149, 151, 15; 558/154; 562/432, 439, 503, 505, 509, 511, 556, 560; 556/407, 419, 421

[56] References Cited

U.S. PATENT DOCUMENTS

| | | | |
|---|---|---|---|
| T858,009 | 1/1969 | Tholstrup et al. | 524/194 |
| T945,001 | 4/1976 | Dexter | 524/194 |
| 3,661,912 | 5/1972 | Kalz et al. | 760/281 |
| 3,678,005 | 7/1972 | Rabilloud et al. | 260/47 |
| 3,699,074 | 8/1970 | Lubowitz et al. | 260/37 |
| 3,734,885 | 5/1973 | Muller et al. | 564/151 |
| 3,821,162 | 6/1974 | Dexter | 524/94 |
| 3,904,581 | 9/1975 | Murayama et al. | 524/99 |
| 3,933,736 | 1/1976 | Yoshikawa et al. | 524/94 |
| 3,956,331 | 5/1976 | Yoshikawa et al. | 524/105 |
| 4,116,930 | 9/1978 | Dexter et al. | 524/99 |
| 4,212,880 | 7/1980 | Fisher et al. | 424/274 |
| 4,223,147 | 9/1980 | Oertel et al. | 524/103 |
| 4,356,307 | 10/1982 | Kelkenberg et al. | 524/103 |
| 4,464,240 | 8/1984 | Hansen | 548/475 |
| 4,506,047 | 3/1985 | Witman et al. | 524/94 |
| 4,520,146 | 5/1985 | Hansen | 548/475 |
| 4,581,396 | 4/1986 | Sonnenberg | 524/89 |
| 4,594,375 | 6/1986 | Krishnan et al. | 524/94 |
| 4,638,072 | 1/1987 | Fields et al. | 549/235 |
| 4,730,017 | 3/1988 | Avar | 524/99 |
| 4,785,063 | 11/1988 | Slongo et al. | 548/261 |

FOREIGN PATENT DOCUMENTS 2174093 10/1986 United Kingdom .

*Primary Examiner*—Veronica P. Hoke
*Attorney, Agent, or Firm*—Panitch, Schwarze, Jacobs and Nadel

[57] ABSTRACT

The present invention comprises reaction products resulting from the reaction of hydrazido-substituted or certain amino-substituted polymer stabilizers and cyclic dianhydrides, as well as the use of such products. The polymer stabilizers of the invention are useful for protecting a large variety of synthetic polymeric organic materials from the degradative effects of heat, light and oxygen. Some of the modifiers are flame retardants and many are metal deactivators in addition to their primary activity.

24 Claims, No Drawings

DIANHYDRIDE COUPLED POLYMER STABILIZERS

BACKGROUND OF THE INVENTION

1. Field of the Invention

This invention relates to additive modifiers for synthetic polymers or polymer blends that protect such materials against the effects of photooxidative and/or thermooxidative degradation and, in some instances, provide flame retardant properties to the synthetic polymers with which they are blended. The term "stabilizer" as used herein generally includes the various antioxidizing, heat stabilizing, light stabilizing, flame retarding, and metal deactivating properties of compounds with which the term is used. The novel stabilizers of the invention are based on the products of the reaction of hydrazido-substituted or certain amino-substituted stabilizer species with cyclic dianhydrides.

2. Description of the Prior Art

It is well known that organic polymeric materials are subject to degradation by the chemical action of light, heat and oxygen. This degradation is manifested by color development and loss of physical properties. To overcome these problems, polymers are normally protected by the incorporation of many types of thermal stabilizers, photostabilizers and antioxidant compounds.

Some stabilizer additives prepared from pyromellitic dianhydride are known. U.S. Pat. No. 4,116,930 describes the preparation of pyromellitic diimide derivatives of 3,5-dialkyl-4-hydroxyphenyl substituted amines. The compounds are used as antioxidant stabilizers for a variety of organic polymeric substances.

U.S. Pat. No. 3,821,162 discloses that certain diimide antioxidant stabilizers have also been prepared from benzophenone-3,3',4,4'-tetracarboxylic acid dianhydride and 3,5-dialkyl-4-hydroxyphenyl substituted amines.

U.S. Pat. No. 3,904,581 discloses the pyromellitic diimide derivative of 4-amino-2,2,6,6-tetramethylpiperidine. This is an example of a hindered amine light stabilizer (HALS) diimide, useful for protecting polymeric substances from photochemical degradation.

U.S. Pat. No. 4,594,375 teaches the use of pyromellitic diimide aryl sulfonate salts as flame retardants for aromatic thermoplastic polycarbonates.

U.S. Pat. No. 4,506,047 discloses the products of the reaction of pyromellitic dianhydride with alkyl amines forming bis-pyromellitic derivatives that, when added to polycarbonate resins, provide compositions with improved physical properties.

As disclosed in U.S. Pat. No. 3,661,912, certain hydrazides have been reacted with 3,4,9,10-perylene-tetracarboxylic dianhydride for use as non-fading dye compositions. However these compositions were not stabilizer additives for polymers.

U.S. Pat. No. 4,212,880 discloses acyl amino-substituted pyromellitic diimides as feed additives for agricultural applications. Use of these derivatives was not contemplated for the stabilization of organic polymeric materials. None of the compounds prepared contained recognizable photostabilizers or thermal stabilizer groups.

U.S. Pat. No. 3,956,331 describes the reaction of salicyloyl hydrazine with many anhydride compounds including pyromellitic dianhydride to produce N-(salicyloylamino)imides. These imide materials are claimed to be stabilizers for polyolefin compositions. A related patent, U.S. Pat. No. 3,933,736, claims these stabilized polyolefin compositions to be resistant to the degradative effects of heavy metals, such as copper.

U.S. Pat. No. 4,581,396 describes the use of pyromellitic diimides as fire retardants for polymers. The additive was prepared by reacting pyromellitic dianhydride with pentabromobenzylamine.

SUMMARY OF THE INVENTION

One aspect of the present invention is a polymer stabilizer compound obtained by the reaction of at least one hydrazido-substituted polymer stabilizer group or certain amino-substituted polymer stabilizer groups with a dianhydride selected from the group consisting of dianhydrides and substituted dianhydrides, wherein the compound includes at least one stabilizer functional group bonded as a N-substituent to a reaction product selected from the group consisting of a diimide and an intermediate amic acid capable of cyclizing to a diimide.

The polymer stabilizer compounds of the present invention have the general formula set forth hereinafter.

Another aspect of the present invention is the use of the novel stabilizer compounds to modify and stabilize host polymers by blending the polymer with an amount of one or more of the stabilizer compounds effective to stabilize the polymer.

In accordance with the invention there is provided a novel class of stabilizer species prepared from the reaction of hydrazido-substituted or certain amino-substituted stabilizer groups with dianhydrides or substituted dianhydrides. The stabilizer functionality is attached as pendant N-substitutents on the resultant diimides or as N-substituents of intermediate amic acids which are capable of cyclizing to the imide groups under appropriate reaction conditions. The resultant novel compositions are useful as thermal and/or photostabilizers, antioxidants and flame retarders for polyolefins, (rubber modified) styrenics, acrylics and engineering thermoplastics such as poly(phenylene oxide), poly(phenylene ether), polycarbonate and poly blends of these and other synthetic polymers. The stabilizers of the present invention are capable of functioning as metal deactivators in addition to their primary activity.

DETAILED DESCRIPTION OF THE PREFERRED EMBODIMENTS

General Formula:

The present invention comprises a compound having a general formula:

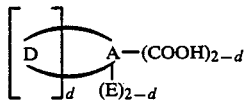

where A is an organic tetravalent radical having at least two carbon atoms, preferably 2 to 48. More particularly A is a linear or branched saturated or unsaturated aliphatic tetravalent radical of 2 to 20 carbons, saturated or unsaturated alicyclic tetravalent radical of 4 to 12 carbons, aralkyl tetravalent radical of 7 to 48 carbons, aralkenyl tetravalent radical of 9 to 48 carbons, an aromatic homocyclic tetravalent radical formed of one ring or two or more (e.g. 2 to 6) fused or linked rings each of which preferably contains 5 to 7 carbons, or an aromatic heterocyclic tetravalent radical formed of one ring or two or more (e.g. 2 to 6) fused or linked rings each of which preferably contains 4 to 6 carbons and optionally containing heteroatoms selected from oxygen, sulfur and nitrogen atoms.

When A is a non-aromatic tetravalent radical, two groups of two valences on adjacent carbon atoms are present to accommodate the one or two D diradical or diradicals and/or the one or two E monovalent radical or radicals and/or the one or two COOH group or groups; and when A is an aromatic tetravalent radical, two groups of two valences in ortho or peri position are present to accommodate the one or two D diradical or diradicals and/or the E monovalent radical or radicals and/or the COOH group or groups.

When A contains several interlinked cycles, the linking members are a direct bond or divalent radical selected from

—O—, —S—, —SO—, —SO$_2$—, —CO—,

—NR$^1$—, —COO—, —CHOR$^1$—, —CF$_2$—, —N=N—,

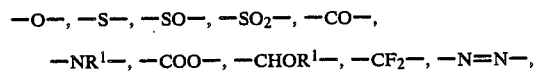

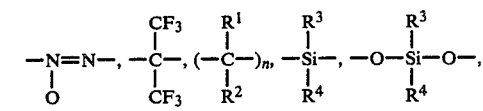

—CO—(R$^1$)N—R$^5$—N(R$^2$)—CO—,

—O—CO—R$^5$—CO—O—, —CO—O—R$^5$—O—CO—,

—(R$^1$)N—CO—N(R$^2$)—, —(R$^1$)N—COCO—N(R$^2$)—,

—CO—N(R$^1$)—, and —O—R$^5$—O—,

R$^1$ and R$^2$ are independently selected from hydrogen, alkyl of 1 to 4 carbons, cycloalkyl of 4 to 7 carbons and phenyl, R$^3$ and R$^4$ are independently chosen from alkyl of 1 to 4 carbons, cycloalkyl of 4 to 7 carbons and phenyl, R$^5$ is selected from linear or branched alkylene of 1 to 12 carbons, cycloalkylene of 5 to 12 carbons and arylene of 5 to 20 carbons, diphenylsulfonyl-4,4,-diyl, diphenylsulfonyl-3,4'-diyl, 4,4'-alkylidenediphenyl-1,1'-diyl of 13 to 21 carbons total and 4,3'-alkylidenediphenyl-1,1'-diyl of 13 to 21 carbons total, and n is an integer of 1 to 4.

Optional substituents for A, R$^1$, R$^2$, R$^3$, R$^4$ and R$^5$ include alkyl of 1 to 4 carbons, alkoxy of 1 to 4 carbons, acyl or acyloxy of 1 to 4 carbons, alkoxycarbonyl of 2 to 5 carbons, arylcarbonyl of 7 to 11 carbons, acryloyloxy, methacryloyloxy, aryloxy of 6 to 10 carbons, aralkyl of 7 to 10 carbons, aryloxycarbonyl of 7 to 11 carbons, phenyl, hydroxy, carboxy, nitrile, chloro, bromo, epoxy, alkylmercapto of 1 to 6 carbons, arylmercapto of 6 to 10 carbons, alkylamino of 1 to 4 carbons, dialkylamino of 2 to 8 carbons, arylamino of 8 carbons, arylalkylamino of 7 to 10 carbons and trialkoxysilyl of 4 to 9 carbons.

Preferably, A is a tetravalent saturated or unsaturated alicyclic radical of 4 to 12 carbons or an aromatic homocyclic radical of one ring or two or more (e.g. 2 to 6) fused or linked rings each of which contains 6 carbons. When aromatic radical A contains several interlinked cycles, the linking members are a direct bond or divalent radical selected from —O—, —S—, —SO—, —CO—, —COO— or —CO—O—R$^5$—O—CO—.

Most preferably, A is a tetravalent saturated or unsaturated alicyclic radical of 4 to 12 carbons or an aromatic homocyclic radical of one ring or two or more (e.g. 2 to 4) fused or linked rings each of which contains 6 carbons, for a total of 6 to 24 carbons. When aromatic radical A contains several interlinked cycles, the linking members are a direct bond or divalent radical selected from —O—, —S—, —CO— or —CO—O—R$^5$—O—CO—.

D is divalent radical —C(=O)—N(G)—C(=O)—(CH$_2$)$_x$—, where x is 0 or 1.

E is monovalent radical —(CH$_2$)$_x$—C(=O)NH—G where x is as previously defined.

d is 0, 1 or 2.

The compound contains two stabilizer groups G which may be the same or different and are chosen from the following list of general structures:

(a) Hindered phenols identified as G$_1$ having the general structure:

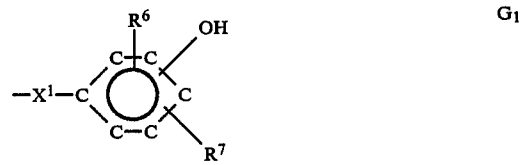

wherein
R$^6$ is t-alkyl of 4 to 8 carbons and must be adjacent to the hydroxy substituent,
R$^7$ is selected from hydrogen, alkyl of 1 to 8 carbons including t-alkyl of 4 to 8 carbons, and alkoxy of 1 to 8 carbons,
X$^1$ is a divalent radical selected from

—N(R)—C(=O)—R$^8$—C(=O)—NH—,

—N(R)—C(=O)—O—R$^9$—,

—N(R)—C(=O)—R$^9$—Z—R$^{10}$—,

—N(R)—C(=O)—R$^9$—, and

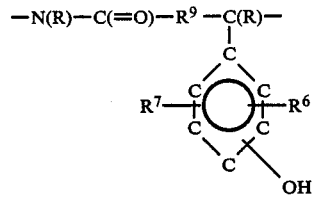

Z is selected from —N(R)—, —S—, —O— and —N(R)—R$^{11}$—N(R)—,

R is selected from hydrogen, primary or secondary alkyl of 1 to 8 carbons, aralkyl of 7 to carbons, and cycloalkyl of 5 to 12 carbons, R$^8$ is selected from a direct bond, alkylene of 1 to 14 carbons, oxydialkylene of 4 to carbons, thiodialkylene of 4 to 10 carbons, alkenylene of 2 to 10 carbons, and o-, m-, and p-phenylene, R$^9$ and R$^{10}$ are independently either a direct bond or alkylene of 1 to 4 carbons, R$^{11}$ is alkylene of 2 to 12 carbons.

In the definitions of X$^1$ above, and X$^2$, X$^3$, X$^4$, X$^5$, X$^6$, X$^7$, and X$^8$ below, the orientation of the radical as written is such that the left end is linked through other atoms to A.

Preferably, in $G_1$ the hydroxy group is in the 4 position, $R^6$ is a t-butyl or t-amyl group in the 3 position of the phenyl ring, $R^7$ is a t-butyl or t-amyl group in the 5 position of the phenyl ring, and $X^1$ is —N(R)—C(=O)—$R^8$—C(=O)—NH—, —N(R)—C(=O)—$R^9$—Z—$R^{10}$— or —N(R)—C(=O)—$R^9$—. Most preferably, $X^1$ is —N(R)—C(=O)—$R^8$—C(=O)—NH— or —N(R)—C(=O)—$R^9$—Z—$R^{10}$.

(b) Hindered amines identified as $G_2$ having the general structure:

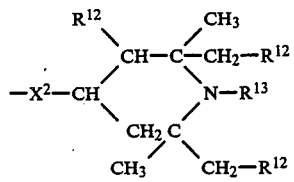

wherein $R^{12}$ is selected from hydrogen and alkyl of 1 to 4 carbons, $R^{13}$ is selected from hydrogen, oxyl, hydroxy, alkyl of 1 to 20 carbons, alkenyl or alkynyl of 3 to 8 carbons, aralkyl of 7 to 12 carbons, aliphatic acyl of 1 to 10 carbons, aromatic acyl of 7 to 13 carbons, alkoxycarbonyl of 2 to 9 carbons, aryloxycarbonyl of 7 to 15 carbons, alkyl, aryl, cycloalkyl or aralkyl substituted carbamoyl of 2 to 13 carbons, hydroxyalkyl of 1 to 5 carbons, 2-cyanoethyl, epoxyalkyl of 3 to 10 carbons and polyalkylene oxide of 4 to 30 carbons, $X^2$ is a divalent radical selected from —N(R)—C(=O)—$R^8$—C(=O)—W—, —N(R)—C(=O)—$R^9$—Z—$R^{10}$—, and —N(R)—C(=O)—$R^9$—, W is selected from —Z—, —N(CH$_2$—CH$_2$—C≡N)—, and a radical of formula

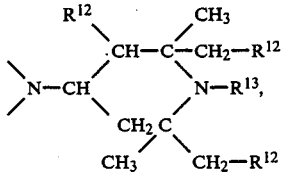

R, $R^8$, $R^9$, $R^{10}$ and Z are as previously defined.

Preferably, $R^{12}$ is hydrogen or methyl, $R^{13}$ is selected from hydrogen, methyl, acetyl, benzoyl, 2-hydroxyethyl or benzyl, $X^2$ is a divalent radical selected from —N(R)—C(=O)—$R^8$—C(=O)—W—, —N(R)—C(=O)—$R^9$—Z—$R^{10}$—, W is —Z— or 2,2,6,6-tetramethyl-4-piperidinyliminyl, Z is —N(R)— or —O—, $R^8$ is a direct bond or alkylene of 1 to 4 carbons, $R^9$ is alkylene of 1 to 3 carbons, $R^{10}$ is a direct bond, $R^{11}$ is alkylene of 2 to 4 carbons.

Most preferably, $R^{12}$ is hydrogen, $R^{13}$ is hydrogen, methyl or acetyl, $X^2$ is a divalent radical selected from —N(R)—C(=O)—$R^8$—C(=O)—W— and —N(R)—C(=O)—$R^9$—Z—$R^{10}$—, Z is —N(R)—, $R^8$ is a direct bond, and $R^9$ is ethylene.

(c) Sulfides identified as $G_3$ having the general structure:

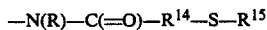

—N(R)—C(=O)—$R^{14}$—S—$R^{15}$      $G_3$ wherein:

$R^{14}$ is alkylene of 1 to 4 carbons, $R^{15}$ is selected from aralkyl of 7 to 12 carbons, alkyl of 1 to 18 carbons and dialkylaminoalkyl of 3 to 12 carbons.

Preferably $R^{14}$ is alkylene of 1 to 2 carbons, $R^{15}$ is alkyl of 6 to 18 carbons, benzyl or dimethylaminoethyl. Most preferably, $R^{15}$ is alkyl of 6 to 12 carbons.

(d) 2-Hydroxybenzophenones identified as $G_4$ having the general structure:

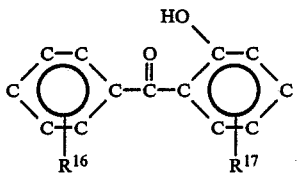

wherein $R^{16}$ and $R^{17}$ are independently selected from hydrogen, hydroxy, alkyl of 1 to 8 carbons, alkoxy of 1 to 8 carbons and a connecting group $X^4$, with the proviso that only one of either $R^{16}$ or $R^{17}$ is the connecting group $X^4$, and $X^4$ is a divalent radical selected from —N(R)—C(=O)—$R^9$—Z—, —N(R)—C(=O)—O—$R^9$—Z—, —$R^{10}$—, —$R^{26}$—O—, —N(R)—C(=O)— and —N(R)—S(=O)$_2$—, R, $R^9$, $R^{10}$ and Z are as previously defined, and $R^{26}$ is alkylene of 1 to 4 carbons.

The aromatic nuclei are optionally substituted with one or more groups selected from hydroxy, alkyl of 1 to 8 carbons, and alkoxy of 1 to 8 carbons.

Preferably, $R^{16}$ is selected from hydrogen, hydroxy, and alkoxy of 1 to 8 carbons, $R^{17}$ is $X^4$, $X^4$ is selected from —N(R)—C(=O)—$R^9$—Z—, —N(R)—C(=O)—O—$R^9$—Z—, and —N(R)—S(=O)$_2$—, $R^9$ is alkylene of 1 to 2 carbons, and Z is —O—. Most preferably, $R^{16}$ is hydrogen, and $X^4$ is selected from —N(R)—C(=O)—$R^9$—Z—, —N(R)—C(=O)—O—$R^9$—Z— and —N(R)—S(=O)$_2$—.

(e) 2-(2-hydroxyphenyl)-2H-benzotriazoles identified as $G_5$ having the general structure:

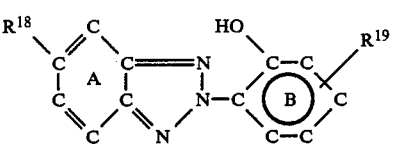

wherein $R^{18}$ is selected from hydrogen, alkyl of 1 to 4 carbons, alkoxy of 1 to 8 carbons, carboxy, alkoxycarbonyl of 2 to 11 carbons, carboxylic acid amide, chlorine, bromine, sulfonic acid, alkylsulfonyl and the connecting group $X^5$, $R^{19}$ is selected from hydrogen, hydroxy, alkyl of 1 to 8 carbons including t-alkyl of 4 to 8 carbons, alkoxy of 1 to 8 carbons, aralkyl of 7 to 12 carbons, aryl of 6 to 14 carbons and the connecting group $X^6$.

Substitution must be such that one and only one of the substituents ($R^{18}$ and $R^{19}$) is the connecting group.

$X^5$ is a divalent radical selected from —N(R)—C(=O)— and —N(R)—S(=O)$_2$—, $X^6$ is a direct bond or divalent radical selected from —N(R)—C(=O)$R^8$—C(=O)—NH—$R^9$—, —N(-

R)—C(=O)—R⁹—Z—R¹⁰—, —N(R)—C(=O)—O—R⁹—, —N(R)—C(=O)—R⁹—, —R¹⁰—, —R²⁶—O—, and —N(R)—C(=O)—, R⁸, R⁹, R¹⁰, R²⁶ and Z are as previously defined.

Aromatic rings A and B are optionally substituted with one or more groups selected from alkyl of 1 to 8 carbons, alkoxy of 1 to 8 carbons, chlorine and bromine.

Preferably, R¹⁸ is hydrogen or chlorine, R¹⁹ is the connecting group X⁶, X⁶ is a divalent radical selected from —N(R)—C(=O)—R⁸—C(=O)—NH—R⁹—, —N(R)—C(=O)—R⁹—, —N(R)—C(=O)—R⁹—Z—R¹⁰— and —R¹⁰—, Z is —N(R)— or —O—, R⁸ is a direct bond or alkylene of 1 to 4 carbons, R⁹ is methylene and R¹⁰ is methylene. Most preferably, R¹⁸ is hydrogen, R⁸ is a direct bond and Z is —N(R).

(f) Aromatic amines identified as G₆ having the general structure:

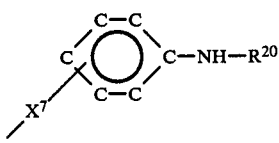

G₆ wherein

R²⁰ is selected from aryl of 6 to 14 carbons, alkyl of 1 to 12 carbons and cycloalkyl of 5 to 12 carbons, X⁷ is a divalent radical selected from —N(R)—C(=O)—R⁸—C(=O)—NH— and —N(R)—C(=O)—R⁹—NH—, R⁸ and R⁹ are as previously defined.

Preferably, R²⁰ is aryl of 6 to 10 carbons or alkyl of 1 to 12 carbons, X⁷ is —N(R)—C(=O)—R⁸—C(=O)—NH—, R⁸ is a direct bond or alkylene of 1 to 4 carbons. Most preferably, R²⁰ is aryl of 6 to 10 carbons and R⁸ is a direct bond.

(g) Heterocyclic stabilizers identified as G₇ having the general structure:

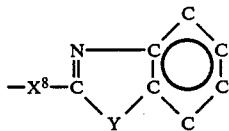

G₇ wherein

X⁸ is a divalent radical selected from —N(R)—C(=O)—R⁹—Z— and —N(R)—C(=O)—R⁸—C(=O)—NH—, Y is selected from —NH— and —S—, R⁸, R⁹ and Z are as previously defined.

The aromatic nucleus is optionally substituted with one or more groups selected from hydroxy, alkyl of 1 to 8 carbons, and alkoxy of 1 to 8 carbons.

Preferably, X⁸ is —N(R)—C(=O)—R⁹—Z—, R⁹ is alkylene of 1 to 3 carbons, Z is —S— or —N(R)—, and R is hydrogen. Most preferably, R⁹ is methylene, and Z is —S—.

(h) Oxanilide derivatives identified as G₈ having the general structure:

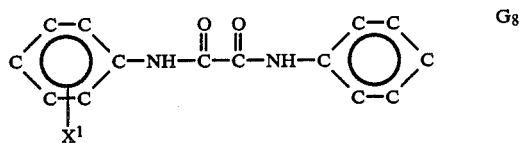

G₈ wherein

X¹, R⁸, R⁹, R¹⁰ and Z are as previously defined.

Additional substituents on the aromatic nuclei include alkyl of 1 to 8 carbons, alkoxy of 1 to 4 carbons and halogen.

Preferably X¹ is —N(R)—C(=O)—R⁸—C(=O)—NH—, —N(R)—C(=O)—R⁹—Z—R¹⁰— or —N(R)—C(=O)—R⁹—. Most preferably, X¹ is —N(R)—C(=O)—R⁸—C(=O)—NH— or —N(R)—C(=O)—R⁹—Z—R¹⁰—.

(i) Halogen containing amide derivatives identified as G₉ having the general structure:

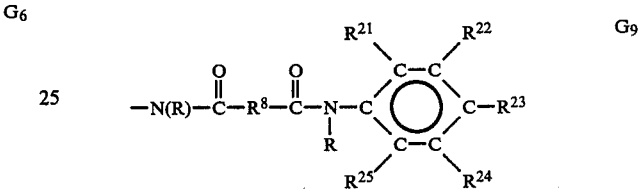

G₉ wherein

R²¹, R²², R²³, R²⁴, and R²⁵ are independently selected from hydrogen, chlorine, bromine, hydroxy, alkoxy or alkylthio of 1 to 12 carbons, acyloxy or acylthio of 6 to 12 carbons, aryl of 6 to 12 carbons, alkyl of 1 to 8 carbons, aralkyl of 7 to 13 carbons, and alkoxycarbonyl of 1 to 8 carbons, with the proviso that at least one of R²¹, R²², R²³, R²⁴, and R²⁵ must be chlorine or bromine, and R and R⁸ are as previously defined.

Preferably, R²¹, R²², R²³, R²⁴, and R²⁵ are independently selected from hydrogen, chlorine or bromine, alkyl of alkoxy of 1 to 4 carbons, and aralkyl of 7 to 13 carbons. Most preferably, R²¹, R²², R²³, R²⁴, and R²⁵ are independently selected form hydrogen, chlorine or bromine.

Illustrative examples of specific stabilizer compounds according to the present invention include the following, without limitation:

1. N,N′-bis[3-(3,5-di-t-butyl-4-hydroxyphenyl)-propanamido]-3,6-dibromopyromellitimide
2. N,N′-bis[N′-1,2,2,6,6-pentamethylpiperidin-4-yl)oxamido]pyromellitimide
3. N,N′-bis[3-dodecylthiopropylamido]pyromellitimide
4. N,N′-bis[4-benzoyl-3-hydroxyphenoxyacetamido]-pyromellitimide
5. N,N′-bis[4-(2H-benzotriazol-2-yl)-2-hydroxyphenoxy-acetylamido]pyromellitimide
6. N,N′-bis[N′-p-anilinophenyloxamido]pyromellitimide
7. N,N′-bis[benzothiazol-2-ylmercaptoacetamido]-pyromellitimide
8. N,N′-bis[N′-(2,4,6-tribromophenyl)oxamido]-pyromellitimide
9. N,N′-bis[3,5-di-t-butyl-4-hydroxybenzylmercaptoacetamido]pyromellitimide
10. N-[3-(3,5-di-t-butyl-4-hydroxyphenyl)-propanamido]-N′-(3hexylthiopropylamido)pyromellitimide 11. N,N-bis[3-(3-methyl-5-t-butyl-4-hydroxyphenyl)-propanamido]pyromellitimide
12. N,N'-bis[3-(3,5-di-t-butyl-4-hydroxyphenyl)-propanamido]3,3',4,4'-biphenyltetracarboxylic diimide
13. N,N'-bis[3-(3,5-di-t-butyl-4-hydroxyphenyl)-propanamido]-(3,4-dicarboxyphenyl)ether diimide
14. N,N'-bis(3-hexylthiopropylamido)-3,4,9,10-perylenetetracarboxylic diimide
15. N,N'-bis[3-(3,5-di-t-butyl-4-hydroxyphenyl)-propanamido]bicyclo[2.2.2]oct-7-ene-2,3,5,6-tetracarboxylic diimide
16. 4,4'-(4-acetoxy-2,6-dioxa-1,7-dioxoheptane-1,7-diyl)bis[N-(3-[3,5-di-t-butyl-4-hydroxyphenyl]-propanamido)phthalimide]
17. 4,4'-(2,5-dioxa-1,6-dioxohexane-1,6-diyl)bis[N-(3-hexylthiopropylamido)phthalimide]
18. 2-[3-(3,5-di-t-butyl-4-hydroxyphenyl)propanamido]-3a,4,5,7a-tetrahydro-6-methyl-5-[1-(3-[3,5-di-t-butyl-4-hydroxyphenyl]propanamido)-2,5-dioxopyrrolidin-3-yl]-1H-isoindole-1,3(2H)-dione
19. 2-(3-hexylthiopropylamido)-3a,4,5,7a-tetrahydro-7-methyl-5-[1-(3-hexylthiopropylamido)-2,5-dioxopyrrolidin-3-yl]-1H-isoindole-1,3(2H)-dione
20. N-[3-(3-(2H-benzotriazol-2-yl)-4-hydroxy-5-t-butyl-phenyl)propanamido]-N'-[N'-(2,2,6,6-tetramethyl-4-piperidinyl)oxamido]pyromellitimide
21. N,N'-bis[3-(3-(2H-benzotriazol-2-yl)-4-hydroxy-5-t-butylphenyl)propanamido]pyromellitimide
22. N,N'-bis[3,3-di-(3-t-butyl-4-hydroxyphenyl)-butanamido]pyromellitimide.

Utility

The inventive stabilizers may be blended with many types of polymers to produce stabilized or modified polymers. Examples of polymers and copolymers which may be stabilized by the polymer stabilizers of the present invention include, without limitation:

1. Polyolefins, such as high, low and linear low density polyethylenes, which may be optionally cross-linked, polypropylene, polyisobutylene, poly(methylbutene-1), polyacetylene, and in general polyolefins derived from monomers having from two to about ten carbons and mixtures thereof.
2. Polyolefins derived from diolefins, such as polybutadiene and polyisoprene.
3. Copolymers of mono or diolefins, such as ethylene-propylene, propylene-butene-1, propylene-isobutylene and ethylene-butene-1 copolymer.
4. Terpolymers of ethylene and propylene with dienes (EPDM), such as butadiene, hexadiene, dicyclopentadiene and ethylidene norbornene.
5. Copolymers of alpha-olefins with acrylic acid or methacrylic acids or their derivatives, such as ethylene-acrylic acid, ethylene-methacrylic acid and ethylene-ethyl acrylate copolymers.
6. Styrenic polymers, such as polystyrene (PS) and poly(p-methylstyrene).
7. Styrenic copolymers and terpolymers, such as styrene-butadiene (SBR), styrene-allyl alcohol and styrene-acrylonitrile (SAN), styrene-acrylonitrile-methacrylate terpolymer, styrene-butadiene-styrene block copolymers (SBS), rubber modified styrenics, such as styrene-acrylonitrile copolymers modified with acrylic ester polymer (ASA), graft copolymers of styrene on rubbers such as polybutadiene (HIPS), polyisoprene or styrene-butadiene-styrene block copolymers (Stereon TM products available from Firestone Synthetic Rubber and Latex Co.), graft copolymers of styrene-acrylonitrile on rubbers, such as butadiene (ABS), polyisoprene or styrene-butadiene-styrene block copolymers, graft copolymers of styrene-methyl methacrylate on rubbers, such as polybutadiene (MBS), butadiene-styrene radial block copolymers (e.g. KRO 3 of Phillips Petroleum Co.), selectively hydrogenated butadiene-styrene block copolymers (e.g. Kraton G from Shell Chemical Co.) and mixtures thereof.
8. Polymers and copolymers derived from halogen-containing vinyl monomers, such as poly(vinyl chloride), poly(vinyl fluoride), poly(vinylidene chloride), poly(vinylidene fluoride), poly(tetrafluoroethylene) (PTFE), vinylchloride-vinyl acetate copolymers, vinylidene chloride-vinyl acetate copolymers and ethylene-tetrafluoroethylene copolymers.
9. Halogenated rubbers, such as chlorinated and/or brominated butyl rubbers or polyolefins and fluoroelastomers.
10. Polymers and copolymers derived from alpha, beta-unsaturated acids, anhydrides, esters, amides and nitriles or combinations thereof, such as polymers or copolymers of acrylic and methacrylic acids, alkyl and/or glycidyl acrylates and methacrylates, acrylamide and methacrylamide, acrylonitrile, maleic anhydride, maleimide, the various anhydride containing polymers and copolymers described in this disclosure, copolymers of the above polymers and various blends and mixtures thereof as well as rubber modified versions of the above polymers and copolymers.
11. Polymers and copolymers derived from unsaturated alcohols or their acylated derivatives, such as poly(vinyl alcohol), poly(vinyl acetate), poly(vinyl stearate), poly(vinyl benzoate), poly(vinyl maleate), poly(vinyl butyral), poly(allyl phthalate), poly(allyl diethylene glycol carbonate) (ADC), ethylene-vinyl acetate copolymer and ethylene-vinyl alcohol copolymers.
12. Polymers and copolymers derived from unsaturated amines, such as poly(allyl melamine).
13. Polymers and copolymers derived from epoxides, such as polyethylene oxide, polypropylene oxide and copolymers thereof, as well as polymers derived from bis-glycidyl ethers.
14. Poly(phenylene oxides), poly(phenylene ethers) and modifications thereof containing grafted polystyrene or rubbers, as well as their various blends with polystyrene, rubber modified polystyrenes or nylon.
15. Polycarbonates and especially the aromatic polycarbonates, such as those derived from phosgene and bisphenols such as bisphenol-A, tetrabromobisphenol-A and tetramethylbisphenol-A.
16. Polyester derived from dicarboxylic acids and diols and/or hydroxycarboxylic acids or their corresponding lactones, such as polyalkylene phthalates (e.g. polyethylene terephthalate (PET), polybutylene terephthalate (PBT), and poly(1,4-dimethylcyclohexane terephthalate) or copolymers thereof) and polylactones, such as polycaprolactone.
17. Polyarylates derived from bisphenols (e.g.bisphenol-A) and various aromatic acids, such as isophthalic and terephthalic acids or mixtures thereof.
18. Aromatic copolyestercarbonates having carbonate, as well as ester linkages present in the backbone of the polymers, such as those derived from bisphenols, iso- and terephthaloyl chlorides and phosgene.
19. Polyurethanes and polyureas.

20. Polyacetals, such as polyoxymethylenes and polyoxymethylenes which contain ethylene oxide as a comonomer.

21. Polysulfones, polyethersulfones andpolyimidesulfones.

22. Polyamides and copolyamides which are derived from diamines and dicarboxylic acids and/or from aminocarboxylic acids or the corresponding lactones, such as the following nylons: 6, 6/6, 6/10, 11 and 12.

23. Polyimides, polyetherimides, polyamideimides and copolyetheresters.

24. Crosslinked polymers which are derived from aldehydes on the one hand and from phenols, ureas and melamine on the other hand, such as phenol-formaldehyde, urea-formaldehyde and melamine-formaldehyde resins.

25. Alkyl resins such as glycerolphthalic acid resins and mixtures thereof with melamine-formaldehyde resins.

26. Blends of vinyl monomers and unsaturated polyester resins which are derived from copolyesters of saturated and unsaturated dicarboxylic acids with polyhydric alcohols, as well as from vinyl compounds (crosslinking agents) and also halogen-containing, flame resistant modifications thereof.

27. Natural polymers such as cellulose, natural rubber as well as the chemically modified homologous derivatives thereof such as cellulose acetates, cellulose propionate, cellulose butyrate and the cellulose ethers, such as methyl and ethyl cellulose.

In addition, the stabilizers of this invention may be used to stabilize various combinations or blends of the above polymers or copolymers. The stabilized polymers are prepared by mixing or blending with the polymer or copolymer to be stabilized a stabilizer of the present invention, alone or with other desired stabilizers, in amounts sufficient to provide a stabilizing effect. Use levels for the stabilizers of this invention range from about 0.01% to about 10% by weight of the polymer being stabilized, and preferably between about 0.05% and about 2%. One of ordinary skill in the art could readily determine the effective amount of the particular stabilizer and the best blending conditions without undue experimentation.

Other additives can be used in conjunction with the stabilizers of this invention. Non-limiting examples include other antioxidants, such as alkylated monophenols, alkylated hydroquinones, hydroxylated thiodiphenyl ethers, alkylidene-bis-phenols, hindered phenolic benzyl compounds, acylaminophenols, esters of 3-(3,5-di-t-butyl-4-hydroxyphenyl)propionic acid, esters of 3-(5-t-butyl-4-hydroxy-3-methylphenyl)propionic acid, 3-(3,5-di-t-butyl-4-hydroxyphenyl)propionic acid amides; other UV absorbers and light stabilizers, such as 2-(2'-hydroxyphenyl)-2H-benzotriazoles, 2-hydroxybenzophenones, benzylidene malonate esters, esters of substituted or unsubstituted benzoic acids, diphenyl acrylates, nickel chelates, oxalic acid diamides, other hindered amine light stabilizers other additives such as metal deactivators, phosphites and phosphonites, peroxide decomposers, fillers and reinforcing agents, plasticizers, lubricants, corrosion and rust inhibitors, emulsifiers, mold release agents, pigments, carbon black, fluorescent brighteners, organic and inorganic flame retardants and non-dripping agents, melt flow improvers and antistatic agents.

General Preparative Methods.

The novel coupled stabilizers of this invention are prepared from dianhydrides by reacting one or more stabilizers bearing reactive hydrazido or certain amino functional groups with the dianhydrides. In this reaction, the stabilizers become attached in the form of substituted amide groups or substituted imide groups.

Functionalized Hindered Phenol Antioxidants.

(Derived from radical $G_1$).

Examples of hindered phenols which may be reacted with the dianhydrides to produce antioxidant stabilizer compounds include, but are not limited to, the following:

3-(3,5-di-t-butyl-4-hydroxyphenyl)propionhydrazide,
3-(3,5-di-t-amyl-4-hydroxyphenyl)propionhydrazide,
3,(3-t-butyl-5-methyl-4-hydroxyphenyl)propionhydrazide,
3-(3-t-butyl-4-hydroxyphenyl)propionhydrazide,
3-(3,6-di-t-hexyl-4-hydroxyphenyl)propionhydrazide,
3,5-di-t-butyl-4-hydroxybenzhydrazide,
3,5-di-t-amyl-4-hydroxybenzhydrazide,
3-t-butyl-5-methyl-4-hydroxybenzhydrazide,
3-(3,5-di-t-butyl-4-hydroxyphenyl)acrylic acid hydrazide,
4-(3,5-di-t-butyl-4-hydroxyphenyl)semicarbazide,
1-methyl-3-(3,5-di-t-butyl-4-hydroxyphenyl)propionhydrazide,
(3,5-di-t-butyl-4-hydroxyphenyl)acetylhydrazide,
N-(3,5-di-t-butyl-4-hydroxyphenyl)-N'-aminooxamide,
2,5-di-t-butyl-4-hydroxyphenylcarbazate,
3,5-di-t-butyl-4-hydroxybenzylcarbazate,
(3,5-di-t-butyl-4-hydroxyphenylmercapto)acetylhydrazide,
(3-t-butyl-5-methyl-4-hydroxyphenylmercapto)acetylhydrazide,
3-(3,5-di-t-butyl-4-hydroxyphenylmercapto)propionhydrazide,
3-(3-t-butyl-5-methyl-4-hydroxyphenylmercapto)propionhydrazide,
(3,5-di-t-butyl-4-hydroxybenzylmercapto)acetylhydrazide,
(3-t-butyl-5-methyl-4-hydroxybenzylmercapto)acetylhydrazide,
(3-(3,5-di-t-butyl-4-hydroxybenzylmercapto)propionhydrazide,
3,3-di-(3-t-butyl-4-hydroxyphenyl)butanoic acid hydrazide,
3-(3-t-butyl-5-methyl-4-hydroxybenzylmercapto)propionhydrazide.

Functionalized Hindered Amine Light Stabilizers.

(Derived from radical $G_2$).

Hindered amines which may be reacted with the dianhydrides to produce light stabilizer compounds include the following non-exclusive examples:

3-(2,2,6,6-tetramethyl-4-piperidinylamino)propionhydrazide,
(2,2,6,6-tetramethyl-4-piperidinylamino)acetylhydrazide,
3-(1,2,2,6,6-pentamethyl-4-piperidinylamino)propionhydrazide,
N-(2,2,6,6-tetramethyl-4-piperidinyl)hydrazinecarboxamide,
N-(1,2,2,6,6-pentamethyl-4-piperidinyl)hydrazinecarboxamide, N-(2,2,6,6-tetramethyl-4-piperidinyl)-N'-aminooxamide,
N-(1,2,2,6,6-pentamethyl-4-piperidinyl)-N'-aminooxamide,
N-(2,2,6,6-tetramethyl-4-piperidinyl)-N'-aminosuccinamide,
N-(2,2,6,6-tetramethyl-4-piperidinyl)-N'-aminomalonamide,
N-(1-acetyl-2,2,6,6-tetramethyl-4-piperidinyl)-N'-aminooxamide,
3-(1-acetyl-2,2,6,6-tetramethyl-4-piperidinylamino)propionylhydrazide,
(2,2,6,6-tetramethyl-4-piperidinyloxy)acetyl hydrazide,
(1,2,2,6,6-pentamethyl-4-piperidinyloxy)acetylhydrazide,
3-(2,2,6,6-tetramethyl-4-piperidinyloxy)propionylhydrazide,
3-(1,2,2,6,6-pentamethyl-4-piperidinyloxy)propionylhydrazide.

Functionalized Sulfide Antioxidants.

(Derived from radical $G_3$).

Sulfides which may be reacted with the dianhydrides to produce antioxidant stabilizer compounds include the following non-exclusive examples:
3-(methylmercapto)propionhydrazide,
3-(ethylmercapto)propionhydrazide,
3-(butylmercapto)propionhydrazide,
3-(n-hexylmercapto)propionhydrazide,
3-(n-octylmercapto)propionhydrazide,
3-(decylmercapto)propionhydrazide,
3-(dodecylmercapto)propionhydrazide,
3-(stearylmercapto)propionhydrazide,
3-(benzylmercapto)propionhydrazide,
(methylmercapto)acetylhydrazide,
(ethylmercapto)acetylhydrazide,
(benzylmercapto)acetylhydrazide,
(2-(dimethylamino)ethylmercapto)acetylhydrazide.

Functionalized 2-Hydroxybenzophenone Light Stabilizers.

(Derived from radical $G_4$).

2-Hydroxybenzophenones which may be reacted with the dianhydrides to produce light stabilizer compounds include the following non-exclusive examples:
(4-benzoyl-3-hydroxyphenoxy)acetylhydrazide,
(4-(2-hydroxybenzoyl)-3-hydroxyphenoxy)acetylhydrazide,
(4-(4-methoxybenzoyl)-3-hydroxyphenoxy)acetylhydrazide,
(4-(4-benzoyl-3-hydroxyphenoxy)butenoic acid hydrazide,
2-(2',4'-dihydroxybenzoyl)benzoic hydrazide,
2-(2'-hydroxy-4'-methoxybenzoyl)benzoic hydrazide,
2-hydroxy-4-(aminomethyl)benzophenone,
2-hydroxy-4-(2-aminoethyl)benzophenone,
2-hydroxy-4-(2-aminoethoxy)benzophenone.

Functionalized 2-(2-Hydroxyphenyl)-2H-benzotriazole Light Stabilizers.

(Derived from radical $G_5$).

2-(2-Hydroxyphenyl)-2H-benzotriazoles which may be reacted with the dianhydrides to produce light stabilizer compounds include the following non-exclusive examples:
3-(3-(2H-benzotriazol-2-yl)-2-hydroxy-5-t-butylphenyl)propionhydrazide,
3-(3-(5-chloro-2H-benzotriazol-2-yl)-2-hydroxy-5-t-butylphenyl)propionhydrazide,
3-(3-(2H-benzotriazol-2-yl)-2-hydroxy-5-methylphenyl)propionhydrazide,
3-(3-(2H-benzotriazol-2-yl)-2,6-dihydroxyphenyl)propionhydrazide,
3-(3-(5-chloro-2H-benzotriazol-2-yl)-2-hydroxy-5-methylphenyl)propionhydrazide,
(4-(2H-benzotriazol-2-yl)-3-hydroxyphenoxy)acetylhydrazide,
(4-(5-methoxy-2H-benzotriazol-2-yl)-3-hydroxyphenoxy)acetylhydrazide,
(4-(5-chloro-2H-benzotriazol-2-yl)-3-hydroxyphenoxy)acetylhydrazide,
3-(2H-benzotriazol-2-yl)-4-hydroxybenzoic acid hydrazide,
3-(3-(2H-benzotriazol-2-yl)-4-hydroxy-5-t-butylphenyl)propionhydrazide,
2-(2-hydroxy-3-aminomethyl-5-methylphenyl)-2H-benzotriazole,
2-(2-hydroxy-5-aminophenyl)-2H-benzotriazole,
2-(2-hydroxy-4-(3-aminopropoxy)phenyl)-2H-benzotriazole.

Functionalized Aromatic Amine Antioxidants.

(Derived from radical $G_6$).

Secondary aromatic amines which may be reacted with the dianhydrides to produce antioxidant stabilizer compounds include the following non-exclusive examples:
N-p-anilinophenyl oxamic acid hydrazide,
N-p-anilinophenyl succinamic acid hydrazide.

Functionalized Heterocyclic Heat Stabilizers.

(Derived from radical $G_7$).

Benzothiazoles and benzimidazoles which may be reacted with the dianhydrides to produce heat stabilizer compounds, and with the mercapto groups, also an antioxidizing effect, include the following non-exclusive examples:
(benzothiazol-2-ylmercapto)acetylhydrazide,
(benzimidazol-2-ylmercapto)acetylhydrazide.

Functionalized Oxanilide Stabilizers.

(Derived from radical $G_8$).

Oxanilides generally are light stabilizers by virtue of the phenyl groups, although the oxamide groups also provide heat stabilizing and metal deactivating functions. Oxanilides which may be reacted with the dianhydrides to produce compounds having the above-indicated stabilizing effects include the following non-exclusive examples:
N-4-(hydrazinocarbonyl)phenyl-N'-phenyloxamide,
N-4-(hydrazinocarbonyl)phenyl-N'-(4-methoxyphenyl)oxamide,
N-4-(hydrazinocarbonyl)phenyl-N'-(4-bromophenyl)oxamide,
N-2-(hydrazinocarbonyl)phenyl-N'-(4-methylphenyl)oxamide,
N-2-(hydrazinocarbonyl)phenyl-N'-(2,6-dibromophenyl)oxamide,
N-4-(hydrazinocarbonyloxy)phenyl-N'-phenyloxamide,
N-4-(4-hydrazino-4-oxo-2-thiabutyl)phenyl-N'-phenyloxamide,
N-4-(3-hydrazino-3-oxopropyl)phenyl-N'-(2-methoxyphenyl)oxamide.

Functionalized Halogen Containing Amide Flame Retardants.

(Derived from radical G9).

Amides which may be reacted with the dianhydrides to produce flame retardant compounds include the following non-exclusive examples:
N-(2,4,6-trichlorophenyl)-N'-aminooxamide,
N-(2,4,6-tribromophenyl)-N'-aminooxamide,
N-(4-chlorophenyl)-N'-aminooxamide,
N-(4-bromophenyl)-N'-aminooxamide,
N-(4-bromo-2-methoxyphenyl)-N'-aminooxamide,
N-(4-bromo-2-methylphenyl)-N'-aminooxamide,
4-oxo-4-(2,4,6-tribromoanilino)butanoic acid hydrazide,
6-oxo-6-(2,4,6-tribromoanilino)hexanoic acid hydrazide,
10-oxo-10-(2,4,6-tribromoanilino)decanoic acid hydrazide.

Numerous other examples of functionalized stabilizers will be obvious to those skilled in the art.

The stabilizers of the invention are prepared by combining cyclic dianhydrides with stabilizer molecules containing the hydrazide or certain amine functionality. Depending upon the reactivity of the substrates, temperature and other reaction conditions, a variety of products could be obtained. Under conditions of mild temperature (less than about 75° C.) the hydrazide or amine will in most cases react with the dianhydride(s) of the substrate to form stabilizer substituted amidic (or amic) acids. Under conditions of higher temperatures (above about 75° C.) the initially formed amic acid intermediates cyclize to give stabilizer substituted amido imides or imides.

The reaction is typically carried out in an inert solvent such as dimethyl formamide, ethers, alkane hydrocarbons, xylene, dichlorobenzene or quinoline at reflux temperatures. Imide formation is facilitated also by azeotropic water removal during the reaction.

Usually a particular hydrazide or amine stabilizer class (e.g. antioxidant) is reacted with a given dianhydride substrate to produce the stabilizer substituted imide (or amic acid) within that same stabilizer class. However, it is within the scope of this invention to react multiple hydrazide or certain amine stabilizer classes with a given dianhydride substrate provided that the total equivalents of hydrazide or amine does not exceed the equivalents of available dianhydride. Such a product stabilizer species would afford multifunctional stabilization potential. For example, a photostabilizer and an antioxidant can readily be attached to the same molecule.

Also, it is known that certain stabilizer combinations offer synergistic effects. Such combinations can readily be prepared according to the present invention by adjusting the ratios of individual stabilizer hydrazides to the desired levels and reacting this adjusted ratio with the dianhydride substrate.

The concept of combination stabilizers is also extended to multiple dianhydride substrates, thereby affording the potential for complex modifier systems. Such systems can thus be designed to enhance specific polymer performance and/or physical properties.

The dianhydride substrates used to prepare the stabilizers of this invention include, but are not limited to, the following exemplary compounds:
1,2,4,5-benzenetetracarboxylic dianhydride,
1,4,5,8-naphthalenetetracarboxylic dianhydride,
3,3',4,4'-benzophenonetetracarboxylic dianhydride,
3a,4,5,7a-tetrahydro-6-methyl-5-(tetrahydro-2,5-dioxo-3-furanyl)-1,3-isobenzofurandione,
bicyclo[2.2.2]oct-7-ene-2,3,5,6-tetracarboxylic dianhydride,
3,4,9,10-perylenetetracarboxylic dianhydride,
5-(2,5-dioxotetrahydrofuryl)-3-methyl-3-cyclohexene-1,2-dicarboxylic anhydride,
glycerol acetate bistrimellitate, ethyleneglycol bistrimellitate,
3,3',4,4'-biphenyltetracarboxylic acid dianhydride(3,4-dicarboxyphenyl)ether dianhydride.

A more comprehensive listing of dianhydrides suitable as substrates for the preparation of the compounds of this invention is contained in U.S. Pat. Nos. 3,956,331, 4,638,072 and 3,699,074, the disclosures of which are hereby incorporated herein by reference.

Working Examples

The following specific working examples are intended to illustrate rather than limit the generic concept of the invention.

EXAMPLE 1

N,N'-bis[3-(3,5-di-t-butyl-4-hydroxyphenyl)-propanamido]pyromellitimide 7.20 g (32.0 mmol) of pyromellitic dianhydride and 600 ml of xylene were placed into a 2 liter flask equipped with a magnetic stirring bar and a Dean-Stark assembly in an inert atmosphere ($N_2$). To this were added 18.71 g (64.0 mmol) of 3-(3,5-di-t-butyl-4-hydroxyphenyl)propanoic acid hydrazide with an additional 50 ml (rinse) of xylene. The mixture was warmed with an oil bath. At a bath temperature of 55°-60° C., the slurry thickened markedly. The mixture was warmed to reflux (oil bath temperature approx. 170° C.) and azeotropic water removal was continued for 3 hours. The mixture was cooled, diluted with 600 ml of pentane and filtered to collect the solids. The yellow solids were slurried with 600 ml of heptane and the mixture boiled for about one 1 hour to discharge the yellow color. The slurry was cooled and the solids collected by vacuum filtration. After air drying the cream colored solids on a sheet of paper for 45 minutes, the solids were slurried with 500 ml of hexane and the mixture boiled gently for 20 minutes. The mixture was cooled, the solids collected by vacuum filtration and air dried. A final drying under high vacuum at room temperature for 2 hours gave 23.5 g of off-white solids, M.P. 268°-270° C. IR (KBr): 1750 cm$^{-1}$ (C=O), 3645 cm$^{-1}$ (OH).

EXAMPLE 2

The stabilizer of Example 1 was incorporated into Dow 300-6 polycarbonate resin (PC) through extrusion using a C. W. Brabender, type 125-25 H.C.V. unit at a temperature of 280°-300° C. Two commercial stabilizers, Irganox 1010 and Irganox 1076, as well as a control sample, were also compared. The stabilizers were used at a level of 0.2 phr. To all of the polycarbonate samples including the control was added 0.1 phr Sandostab PEPQ (tetrakis [2,4-di-t-butylphenyl]-4,4'-biphenylenediphosphonite), a phosphorous-containing stabilizer from Sandoz Chemicals. The resin blends were extruded, pelletized and injection molded into tensile bars on a Newbury injection molding unit. The tensile bars were then suspended in an air circulating oven at 140° C. and heat aged for 28 days. Stability was measured by yellowness index checked at 7 day intervals. Color development was monitored using a Gardner Colorgard System/05 colorimeter. The results of the test are shown in the table below. The data clearly indicate that the stabilizer composition of Example 1 is significantly more effective than the two commercial antioxidants for suppressing color formation in polycarbonate resin at elevated temperatures.

| Days at 140° C. | Yellowness Index | | | | |
|---|---|---|---|---|---|
| PC Stabilizer | 0 | 7 | 14 | 21 | 28 |
| 1. Control | 17.2 | 28.6 | 33.9 | 40.9 | 50.0 |
| 2. Irganox 1076* | 18.9 | 28.1 | 33.3 | 39.2 | 47.1 |
| 3. Irganox 1010** | 15.7 | 23.3 | 28.9 | 35.7 | 42.5 |
| 4. Example 1 | 18.7 | 23.5 | 26.6 | 29.6 | 32.2 |

All polycarbonate formulations contain 0.1 phr PEPQ.
All stabilizers used at 0.2 phr level.
*Irganox 1076 is octadecyl 3-(3,5-di-t-butyl-4-hydroxy-phenyl)propionate.
**Irganox 1010 is tetrakis [methylene(3,5-di-t-butyl-4-hydroxyhydro-cinnamate)]methane.

EXAMPLE 3

N,N'-Bis[N'-(2,2,6,6-tetramethylpiperidin-4-yl)oxamido]pyromellitimide.

250 ml xylene were placed into a 500 ml 3-neck flask equipped with a magnetic stirrer, thermometer and a Dean-Stark assembly in an inert atmosphere ($N_2$). The solvent was heated (oil bath) to 100° C. 10.9 g (0.05 mol) of pyromellitic dianhydride were then added to the heated solvent. The mixture was heated to reflux until any water present was collected in the Dean Stark assembly. The mixture was cooled to 120° C. for the addition, in portions, of 25.4 g (0.10 mol) of N-(2,2,6,6-tetramethylpiperidin-4-yl)-N'-aminooxamide. The mixture was refluxed intermittently for a total of 13 hours. Only a small amount (much less than theoretical) of water had been obtained in the Dean-Stark assembly. The slurry was cooled to 100° C. then filtered to collect the solids. These solids were slurried with hexane to remove the xylene and refiltered. After drying, 34.4 g of yellow solids were obtained, M.P. greater than 300° C. IR (KBr) 1680 cm$^{-1}$ (C=O, (s)); 1755 cm$^{-1}$ (C=O, (m)). The carbonyl banding of this sample suggests that the composition of the material is predominantly the amic acid internal salt (1680 cm$^{-1}$) with only a small amount of the diimide (1755 cm$^{-1}$).

EXAMPLE 4

N,N'-Bis(3-n-hexylthiopropylamido)pyromellitimide.

2.67 g (11.85 mmol) of pyromellitic dianhydride and 75 ml of xylene were placed into a 500 ml flask equipped with a magnetic stirring bar and a Dean-Stark assembly in an inert atmosphere ($N_2$). To this, 4.92 g (23.70 mmol) of 3-n-hexylthiopropanoic acid hydrazide along with 65 ml of xylene were added. The stirred slurry was warmed to reflux and azeotropic water removal was continued for 3 hours. The Dean-Stark assembly was replaced with a distillation head and about 80 ml of xylene was allowed to distill off the slurry. The slurry was then cooled to room temperature and diluted with 75 ml of pentane. The solids were collected by vacuum filtration and air dried for 30 minutes. These green-yellow solids were placed into a 200 ml round bottom flask along with 50 ml of nonane. The slurry was heated to boiling and approximately 10 ml of the nonane was allowed to boil off. The slurry was cooled, diluted with pentane and the solids collected by filtration. After high vacuum drying for 20 minutes at room temperature, 7.05 g of yellow solids, M.P. 260°-275° C. IR (KBr): 1675 cm$^{-1}$, 1735 cm$^{-1}$ (both C=O) were obtained.

EXAMPLE 5

N,N'-Bis[3-(3,5-di-t-butyl-4-hydroxyphenyl)-propanamido]-3,3',4,4'-benzophenonetetracarboxylic diimide 1.32 g (4.0 mmol) of 3,3',4,4'-benzophenonetetracarboxylic dianhydride, 2.34 g (8.0 mmol) of 3-(3,5-di-t-butyl-4-hydroxyphenyl)propanoic acid hydrazide and 100 ml of xylene were placed into a 250 ml flask equipped with a magnetic stirring bar and a Dean-Stark assembly in a nitrogen atmosphere. The mixture was refluxed (with water removal) for 1.5 hours, after which time the clear yellow solution was allowed to cool to room temperature. A small amount of mechanical impurities was removed from the solution by filtration. The solvent was evaporated from the filtrate using a rotary stripper and high vacuum pump. There remained about 3.0 g of yellow crystalline solids, M.P. 145°-150° C. IR (cell, CHCl$_3$) 3635 cm$^{-1}$ (OH), 1738 cm$^{-1}$ (C=O).

EXAMPLE 6

N,N'-Bis[3-(3,5-di-t-butyl-4-hydroxyphenyl)-propanamido]-1,4,5,8-naphthalenetetracarboxylic diimide 1.31 g (4 90 mmol) of 1,4,5,8-naphthalenetetra-carboxylic dianhydride, 2.86 g (9.79 mmol) of 3-(3,5-di-t-butyl-4-hydroxyphenyl)propanoic acid hydrazide and 120 ml of xylene were placed into a 250 ml round bottom flask equipped with a magnetic stirring bar and a Dean-Stark assembly in a nitrogen atmosphere. The mixture was refluxed (with water removal) for 6 hours. The reaction remained a yellow slurry throughout this time. The slurry was cooled to about 15° C. and the solids were collected by vacuum filtration. The product was air dried and high vacuum dried to give 4.0 g of light yellow solids, M.P. 300°-303° C. IR (KBr): 3642 cm$^{-1}$ (OH); 1737 cm$^{-1}$, 1702 cm$^{-1}$ (both C=O).

EXAMPLE 7

2-[2-(2,4,6-tribromophenylamino)-2-oxoacetamido]-3a,4,5,7a-tetrahydro-7-methyl-5-[1-(2-[2,4,6-tribromophenylamino]-2-oxoacetamido)-2,5-dioxopyrrollidin-3-yl]-1H-isoindole-1,3(2H)-dione 1.00 g (3.77 mmol) of 5-(2,5-dioxotetrahydro-furyl)-3-methyl-3-cyclohexene-1,2-dicarboxylic anhydride, 3.14 g (7.55 mmol) of N-(2,4,6-tribromophenyl)-N'-aminooxamide and 75 ml of xylene were placed into a 250 ml round bottom flask equipped with a magnetic stirring bar and a Dean-Stark assembly in a nitrogen atmosphere. The mixture was refluxed for 3 hours with water removal. The slurry was cooled to room temperature and the solids collected by vacuum filtration. After high vacuum drying for one hour at room temperature, 3.80 g of white solids, M.P. 210°-215° C. IR (KBr): 1710 cm$^{-1}$, 1740 cm$^{-1}$ (both C=O) were obtained.

EXAMPLE 8

N,N'-Bis[3-(3,5-di-t-butyl-4-hydroxyphenyl)-propanamido]-3,3',4,4'-biphenyltetracarboxylic diimide 1.40 g (4.74 mmol) of 3,3',4,4'-biphenyltetra-carboxylic dianhydride, 2.78 g (9.49 mmol) of 3-(3,5-di-t-butyl-4-hydroxyphenyl)propanoic acid hydrazide and 100 ml of xylene were placed into a 250 ml round bottom flask equipped with a magnetic stirring bar and a Dean-Stark assembly in a nitrogen atmosphere. The mixture was refluxed 2.5 hr. with water removal. The slurry was cooled and the solids collected by vacuum filtration. The wet filter cake was transferred to a 250 ml Erlenmeyer flask and slurried with about 100 ml of hexane. The solids were collected by vacuum filtration, air dried on a sheet of paper, then high vacuum dried for 2 hours at room temperature. 4.12 g of white solids, M.P. 291°–293° C.; IR (KBr): 3640 cm$^{-1}$ (OH); 1690 cm$^{-1}$, 1748 cm$^{-1}$, 1792 cm$^{-1}$ (all C=O) were obtained.

EXAMPLE 9

4,4'-(4-Acetoxy-2,6-dioxa-1,7-dioxoheptane-1,7-hydroxyphenyl]propanamido)phthalimide]

2.32 g (0.0048 mol) of glycerol acetate bistrimellitate and 65 ml of xylene were placed into a 200 ml round bottom flask equipped with a magnetic stirring bar and a Dean-Stark assembly in a nitrogen atmosphere. The mixture did not yield water after being brought to reflux. The reactor was cooled to about 50° C. for the addition of 2.88 g (0.0098 mol) of 3-(3,5-di-t-butyl-4-hydroxyphenyl)propanoic acid hydrazide. Reflux was continued with water removal for one hour. The slightly turbid mixture was then stripped of solvent on a rotary evaporator and high vacuum system. There remained 5.36 g of light yellow solids, M.P. 120°–130° C. IR (KBr): 3640 cm$^{-1}$ (OH); 1750 cm$^{-1}$ (C=O).

EXAMPLE 10

4,4'-(2,5-Dioxa-1,6-dioxohexane-1,6-diyl)-bis-[N-(3-[3,5-di-t-butyl-4-hydroxyphenyl]propanamido)phthalimide]

2.14 g (0.0052 mol) of ethylene glycol bistrimellate and 50 ml of xylene were placed into a 200 ml round bottom flask equipped with a magnetic stirring bar and a Dean-Stark assembly in a nitrogen atmosphere. The mixture did not yield water after being brought to reflux. The reaction was cooled to about 50° C. for the addition of 3.08 g (0.0105 mol) of 3-(3,5-di-t-butyl-4-hydroxyphenyl)propanoic acid hydrazide. Reflux with water removal was then maintained for one hour. The slightly turbid mixture was stripped of solvent on a rotary evaporator and high vacuum system. There remained 5.8 g of yellow solids, M.P. about 100° C. IR(KBr): 3640 cm$^{-1}$ (OH); 1747 cm$^{-1}$ (C=O).

EXAMPLE 11

N,N'-Bis[N'-(2,4,6-tribromophenyl)oxamido]pyromellitimide 1.33 g (0.0059 mol) of pyromellitic dianhydride, 4.92 g (0.0118 mol) of N-(2,4,6-tribromophenyl)-N'-aminooxamide and 120 ml of xylene were placed into a 500 ml round bottom flask equipped with a magnetic stirring bar and a DeanStark assembly in a nitrogen atmosphere. The mixture was refluxed with water removal for 2 hours. The slurry was cooled to near room temperature and vacuum filtered to collect the solids. These solids were reslurried in hot hexane and again collected by filtration. After drying under high vacuum, there remained 6.09 g of chalky white powder, M.P. greater than 300° C. IR(KBr): 1758 cm$^{-1}$, 1715 cm$^{-1}$, 1695 cm$^{-1}$ (all C=O).

EXAMPLE 12

N,N'-bis[N'-(3,5-di-t-butyl-4-hydroxyphenyl)oxamido]-3,3',4,4'-benzophenonetetracarboxylic diimide 1.10 g (0.0033 mol) of 3,3',4,4'-benzophenonetetracarboxylic dianhydride, 2.05 g (0.0066 mol) of 2-(3,5-di-t-butyl-4-hydroxyphenylamino)-2-oxoacetyl hydrazide and 90 ml of xylene were placed into a 200 ml round bottom flask equipped with a magnetic stirring bar and a Dean-Stark assembly and nitrogen atmosphere. The mixture was refluxed with water removal for one hour followed by cooling to room temperature. The resulting suspension was vacuum filtered to collect the solids. The moist filter cake was transferred to a 125 ml Erlenmeyer flask and boiled (with magnetic stirring) in hexane for 15 minutes. The slurry was vacuum filtered to collect the solids which were broken up and air dried overnight. 2.62 g of a pale yellow powder, M.P. about 315° C. IR(KBr): 3640 cm$^{-1}$ (OH); 1749 cm$^{-1}$, 1720 cm$^{-1}$, 1684 cm$^{-1}$ (all C=O) were obtained.

EXAMPLE 13

Preparation of a Mixed Bis N-(Amido)imide Modifier Containing Primary and Secondary Antioxidant Function 1.59 g (0.006 mol) of 5-(2,5-dioxotetrahydro-furyl)-3-methyl-3-cyclohexene-1,2-dicarboxylic anhydride, 0.42 g (0.002 mol) of 3-hexylthiopropanoic acid hydrazide and 50 ml of toluene were placed into a 200 ml round bottom flask equipped with a magnetic stirring bar and a Dean-Stark assembly in a nitrogen atmosphere. The mixture was warmed for 15 minutes in a 100° C. oil bath. After cooling the mixture somewhat, 2.95 g (0.010 mol) of 3-(3,5-di-t-butyl-4-hydroxyphenyl)propanoic acid hydrazide was added along with 25 ml of toluene. The mixture was refluxed (with water removal) for one hour. Solvent was removed on a rotary evaporator and the resulting solids were boiled for 30 minutes in 60 ml of pentane to produce a granular off-white powder. The solids were collected by vacuum filtration. After air drying, there remained 4.79 g of solids, M.P. 140°–160° C. IR (KBr): 3641 cm$^{-1}$ (OH); 1735 cm$^{-1}$ (C=O).

The following mixed amido imides identified as compounds A and B are produced according to the process of this example:

Compound A: 2-[3-(3,5-di-t-butyl-4-hydroxyphenyl)-propanamido]-3a,4,5,7a-tetrahydro-7methyl-5-[1-(3-hexylthiopropylamido)-2,5-dioxopyrrolidin-3-yl]-1H-isoindole-1,3(2H)-dione, Compound B: 2-(3-hexylthiopropylamido)-3a,4,5,7a-tetrahydro-7-methyl-5-{1-[3-(3,5-di-t-butyl-4-hydroxyphenyl)propanamido]-2,5-dioxopyrrolidin-3-yl}-1H-isoindole-1,3(2H)-dione.

In addition to compounds A and B, which may or may not be the principal reaction products, there will be varying amounts of the following compounds C and D formed during the process set forth in this example:

Compound C: 2-(3-hexylthiopropylamido)-3a,4,5,7a-tetrahydro-7-methyl-5-[1-(3-hexylthiopropylamido)-2,5-dioxopyrrolidin-3-yl]-1H-isoindole-1,3(2H)-dione, Compound D: 2-[3-(3,5-di-t-butyl-4-hydroxyphenyl)propanamido]-3a,4,5,7a-tetrahydro-7-methyl-5-{1-[3-(3,5-di-t-butyl-4-hydroxyphenyl)-propanamido]-2,5-dioxopyrrolidin-3-yl}-1H-isoindole-1,3(2H)-dione.

From the foregoing, it should be clear that four products can be obtained from the reaction of this example due to the use of an unsymmetrical dianhydride substrate. If a symmetrical dianhydride had been used (such as pyromellitic dianhydride), the reaction would have yielded only three products. It is not necessary to separate the products from each other before blending with a polymer to be stabilized. The ratio of the particular classes of hydrazido-substituted stabilizers, which react with the dianhydride, is the primary determining factor as to the functionality of the resulting products and product mixtures. Synergistic stabilizing effects are possible by reacting the various particular hydrazido-substituted stabilizer classes with the dianhydrides.

EXAMPLE 14

N,N'-bis[N'-(3,5-di-t-butyl-4-hydroxyphenyl)oxamido]-pyromellitimide 0.85 g (3.76 mmol) of pyromellitic dianhydride, 2.31 g (7.52 mmol) of 2-(3,5-di-t-butyl-4-hydroxyphenylamino)-2-oxoacetyl hydrazide and 130 ml of xylene were placed into a 200 ml flask equipped with a magnetic stirring bar and Dean-Stark assembly, under a nitrogen atmosphere. The mixture was heated to reflux and azeotropic distillation was maintained for 3.5 hr. After cooling to room temperature, the suspended solids were collected by vacuum filtration and rinsed with about 20 ml of pentane. There was obtained 2.59 g of light yellow solids, M.P. >310° C. IR (KBr): 3644 cm$^{-1}$ (OH); 3388 cm$^{-1}$, 3244 cm$^{-1}$ (both NH); 1761 cm$^{-1}$, 1689 cm$^{-1}$ (both C=O).

The present invention may be embodied in other specific forms without departing from the spirit or essential attributes thereof and, accordingly, reference should be made to the appended claims, rather than to the foregoing specification as indicating the scope of the invention.

We claim:

1. A polymer stabilizer compound having a general formula

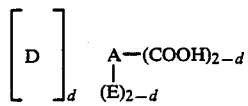

D is divalent radical —C(=O)—N(G)—C(=O)—(CH$_2$)$_x$—, where X is 0 or 1,

E is monovalent radical —(CH$_2$)$_x$—C(=O)NH—G, where x is 0 or 1, d is 0, 1 or 2, A is an organic tetravalent radical of 2 to 48 carbons, when A is a non-aromatic tetravalent radical, two groups of two valences on adjacent carbon atoms are present to accommodate the one or two D diradical or diradicals and/or the one or two E monovalent radical or radicals and/or the one or two COOH group or groups; and when A is an aromatic tetravalent radical, two groups of two valences in ortho or peri position are present to accommodate the one or two D diradical or diradicals and/or the E monovalent radical or radicals and/or the COOH group or groups, and G is a monovalent stabilizer radical selected from the group consisting of (a) hindered phenol-substituted amido, (b) hindered amine-substituted amido, (c) dialkyl sulfide-substituted amido, (d) a compound selected from the group consisting of 2-hydroxybenzophenone-substituted amido and 2-hydroxybenzophenone-substituted alkyl, (e) a compound selected from the group consisting of 2-(2-hydroxyphenyl)-2H-benzotriazole-substituted amido and 2-(2-hydroxyphenyl)-2H-benzoptriazole-substituted alkyl, (f) secondary aromatic amine-substituted amido, (g) a compound selected from the group consisting of benzimidazole-substituted amido and benzothiazole-substiuted amido, (h) oxanilide-substituted amido, (i) halogenated aromatic-substituted amido, and mixtures thereof.

2. The compound of claim 1 in which the hindered phenol-substituted amido group (a) is

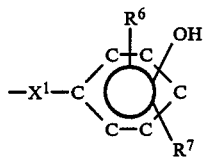

wherein

R$^6$ is t-alkyl to 4 to 8 carbons and must be adjacent to the hydroxy substituent, R$^7$ is selected from the group consisting of hydrogen, alkyl of 1 to 8 carbons including t-alkyl of 4 to 8 carbons, and alkoxy of 1 to 8 carbons, X$^1$ is a divalent radical selected from the group consisting of —N(R)—C(=O)—R$^8$—C(=O)—NH—, —N(R)—C(=O)—O—R$^9$—, —N(R)—C(=O)—R$^9$—Z—R$^{10}$—, and —N(R)—C(=O)—R$^9$—, and —N(R)—C(=O)—R$^9$—, and

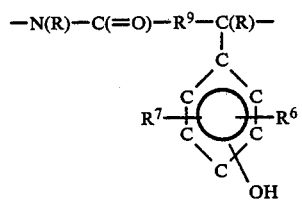

Z is selected from the group consisting of —N(R)—, —S—, —O— and —N(R)—R$^{11}$—N(R)—, R is selected from the group consisting of hydrogen, primary or secondary alkyl of 1 to 8 carbons, aralkyl of 7 to 12 carbons, and cycloalkyl of 5 to 12 carbons, R$^8$ is selected from the group consisting of a direct bond, alkylene of 1 to 14 carbons, oxydialkylene of 4 to 10 carbons, thiodialkylene of 4 to 10 carbons, alkenylene or 2 to 10 carbons, and o-, m- and p-phenylene, R$^9$ and R$^{10}$ are independently selected from the group consisting of a direct bond and alkylene of 1 to 4 carbons, and R$^{11}$ is alkylene of 2 to 12 carbons;

the hindered amine-substituted amido group (b) is

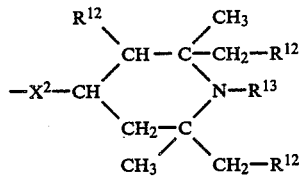

wherein
R¹² is selected from the group consisting of hydrogen and alkyl of 1 to 4 carbons,
R¹³ is selected from hydrogen, oxyl, hydroxy, alkyl of 1 to 20 carbons, alkenyl or alkynyl of 3 to 8 carbons, aralkyl of 7 to 12 carbons, aliphatic acyl of 1 to 10 carbons, aromatic acyl of 7 to 13 carbons, alkoxycarbonyl of 2 to 9 carbons, aryloxycarbonyl of 7 to 15 carbons, alkyl, aryl, cycloalkyl substituted carbamoyl of 2 to 13 carbons, aralkyl substituted carbamoyl of 2 to 13 carbons, hydroxyalkyl of 1 to 5 carbons, 2-cyanoethyl, epoxyalkyl of 3 to 10 carbons and polyalkylene oxide of 4 to 30 carbons,
X² is a divalent radical selected from the group consisting of —N(R)—C(=O)—R⁸—C(=O)—W—, —N(R)—C(=O)—R⁹—Z—R¹⁰— and —N(R)—C(=O)—R⁹—, and
W is selected from the group consisting of —Z—, —N(CH₂—CH₂)—C≡N— and a radical of formula

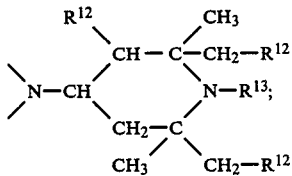

the diakyl sulfide-substituted amido group (c) is

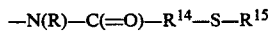
—N(R)—C(=O)—R¹⁴—S—R¹⁵ wherein
R¹⁴ is alkylene of 1 to 4 carbons, and
R¹⁵ is selected from the group consisting of aralkyl of 7 to 12 carbons, alkyl of 1 to 18 carbons and dialkylaminoalkyl of 3 to 12 carbons; the compound selected for the group consisting of the 2-hydroxybenzophenone-substituted amido and 2-hydroxybenzophenone-substituted alkyl groups (d) is

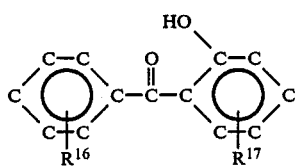

wherein
R¹⁶ and R¹⁷ are independently selected from the group consisting of hydrogen, hydroxy, alkyl of 1 to 8 carbons, alkoxy of 1 to 8 carbons and a connecting group X⁴ with the proviso that only one of either R¹⁶ or R¹⁷ is the connecting group X⁴,
X⁴ is a divalent radical selected from the group consisting of —N(R)—C(=O)—R⁹—Z—, —N(R)—C(=O)—O—R⁹—Z—, —R¹⁰—, —R²⁶—O—, —N(R)—C(=O)— and —N(R)—S(=O)₂—,
R²⁶ is alkylene of 1 to 4 carbons,
and the aromatic nuclei have substituents selected from the group consisting of hydroxy, alkyl of 1 to 8 carbons and alkoxy of 1 to 8 carbons;
the compound selected from the group consisting of 2-(2-hydroxyphenyl)-2H-benzotriazole-substituted amido and 2-(2-hydroxyphenyl)-2H-benzotriazole-substituted alkyl groups (e) is

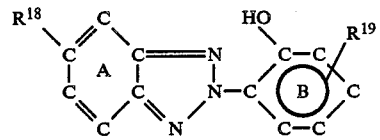

wherein
R¹⁸ is selected from the group consisting of hydrogen, alkyl of 1 to 4 carbons, alkoxy of 1 to 8 carbons, carboxy, alkoxycarbonyl of 2 to 11 carbons, carboxylic acid amide, chlorine, bromine, sulfonic acid, alkylsulfonyl and the connecting group X⁵,
R¹⁹ is selected from hydrogen, hydroxy, alkyl of 1 to 8 carbons including t-alkyl of 4 to 8 carbons, alkoxy of 1 to 8 carbons, aralkyl of 7 to 12 carbons, aryl of 6 to 14 carbons and the connecting group X⁶,
the substitution being such that only one of the substituents R¹⁸ and R¹⁹ is the connecting group,
X⁵ is a divalent radical selected from —N(R)—C(=O)—, —N(R)—S(=O)₂— and
X⁶ is selected from the group consisting of a direct bond and a divalent radical selected from the group consisting of —N(R)—C(=O)—R⁸—C(=O)—N-H—R⁹—, —N(R)—C(=O)—R⁹—Z—R¹⁰—, —N(R)—C(=O)—O—R⁹, —N(R)—C(=O)—R⁹—, —R¹⁰—, —R²⁶—O—, and —N(R)—C(=O)—, and
the aromatic rings A and B have substituents selected from the group consisting of hydrogen, alkyl of 1 to 8 carbons, alkoxy of 1 to 8 carbons, chlorine and bromine;
the secondary aromatic amine-substituted amido group (f) is

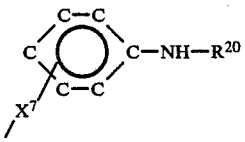

wherein
R²⁰ is selected from the group consisting of aryl of 6 to 14 carbons, alkyl of 1 to 12 carbons and cycloalkyl of 5 to 12 carbons, and
X⁷ is a divalent radical selected from —N(R)—C(=O)—R⁸—C(=O)—NH— and —N(R)—C(=O)—R⁹—NH—;
the compound selected from the group consisting of benzimidazole-substituted amido and benzothiazole-substituted amido groups (g) is

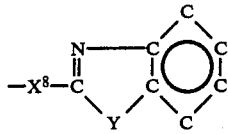

wherein
$X^8$ is a divalent radical selected from the group consisting of —N(R)—C(=O)—R$^9$—Z— and —N(-R)—C(=O)—R$^8$—C(=O)—NH—,
Y is selected from —NH— and —S—, and
the aromatic nucleus has substituents selected from the group consisting of hydrogen, hydroxy, alkyl of 1 to 8 carbons, and alkoxy of 1 to 8 carbons;

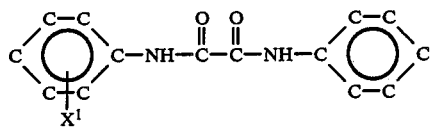

wherein
the aromatic nuclei have substituents selected from the group consisting of hydrogen, alkyl of 1 to 8 carbons, alkoxy of 1 to 4 carbons and halogen;

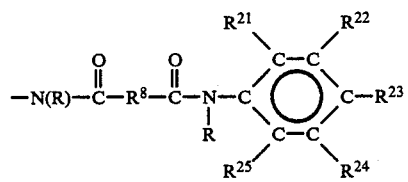

wherein
$R^{21}$, $R^{22}$, $R^{23}$, $R^{24}$, and $R^{25}$ are independently selected from the group consisting of hydrogen, chlorine, bromine, hydroxy, alkoxy or alkylthio of 1 to 12 carbons, acyloxy of 6 to 12 carbons, acylthio of 6 to 12 carbons, aryl of 6 to 12 carbons, alkyl of 1 to 8 carbons, aralkyl of 7 to 13 carbons, and alkoxycarbonyl of 1 to 8 carbons, with the proviso that at least one of $R^{21}$, $R^{22}$, $R^{23}$, $R^{24}$, and $R^{25}$ must be chlorine or bromine;
A is selected from the group consisting of a linear saturated aliphatic tetravalent radical of 2 to 20 carbons, branched saturated aliphatic tetravalent radical of 2 to 20 carbons, linear unsaturated aliphatic tetravalent radical of 2 to 20 carbons, branched unsaturated aliphatic tetravalent radical of 2 to 20 carbons, saturated alicyclic tetravalent radical of 4 to 12 carbons, unsaturated alicyclic tetravalent radical of 4 to 12 carbons, aralkyl tetravalent radical of 7 to 48 carbons, aralkenyl tetravalent radical of 9 to 48 carbons, aromatic homocyclic tetravalent radical formed of one ring or two or more fused or linked rings each of which contains to 7 carbons, and aromatic heterocyclic tetravalent radical formed of one ring or two or more fused or linked rings each of which contains 4 to 6 carbons and optionally containing heteroatom ring members selected from the group consisting of oxygen, sulfur and nitrogen atoms;
and when A contains several interlinked cycles, the linking members are selected from the group consisting of a direct bond and a divalent radical selected from —O—, —S—, —SO—, —SO$_2$—, —CO—, —NR$^1$—, —COO—, —CHOR$^1$—, —CF$_2$—, —N=N—,

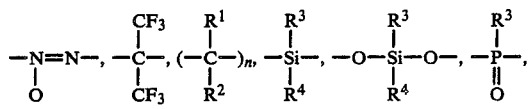

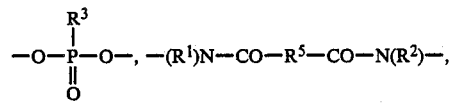

—CO—(R$^1$)N—R$^5$—N(R$^2$)—CO—, —O—CO—R$^5$—CO—O—, —CO—O—R$^5$—O—CO—, —(R$^1$)N—CO—N(R$^2$)—, —(R$^1$)N—COCO—N(R$^2$)—, —CO—N(R$^1$)— and —O—R$^5$—O—, where $R^1$ and $R^2$ are independently selected from the group consisting of hydrogen, alkyl of 1 to 4 carbons, cycloalkyl of 4 to 7 carbons and phenyl,
$R^3$ and $R^4$ are independently selected from the group consisting of alkyl of 1 to 4 carbons, cycloalkyl of 4 to 7 carbons and phenyl, and
$R^5$ is selected for the group consisting of linear alkylene of 1 to 12 carbons, branched alkylene of 1 to 12 carbons, cycloalkylene of 5 to 12 carbons, arylene of 5 to 20 carbons, diphenylsulfonyl-4,4'-diyl, diphenylsulfonyl-3,4'-diyl, 4,4'-alkylidenediphenyl-1,1'-diyl and 4,3'-alkylidenediphenyl-1,1'-diyl, and
n is an integer of 1–4.

3. The compound of claim 1 in which the hindered phenol group (a) is

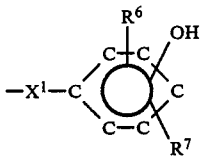

wherein
$R^6$ is t-alkyl of 4 to 8 carbons and must be adjacent to the hydroxy substituent,
$R^7$ is selected from the group consisting of hydrogen, alkyl of 1 to 8 carbons, and alkoxy of 1 to 8 carbons,
$X^1$ is a divalent radical selected from the group consisting of —N(R)—C(=O)—R$^8$—C(=O)—NH—, —N(R)—C(=O)—O—R$^9$—, —N(R)—C(=O)—R$^9$—Z—R$^{10}$—, and —N(R)—C(=O)—R$^9$—, and

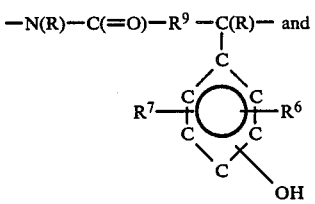

Z is selected from the group consisting of —N(R)—, —S—, —O— and —N(R)—R$^{11}$—N(R)—,
R is selected from the group consisting of hydrogen, primary or secondary alkyl of 1 to 8 carbons, aralkyl of 7 to 12 carbons, and cycloalkyl of 5 to 12 carbons, $R^8$ is selected from the group consisting of a direct bond, alkylene of 1 to 14 carbons, oxydialkylene of 4 to 10 carbons, thiodialkylene of to 10 carbons, alkenylene of 2 to 10 carbons, and o-, m-, and p-phenylene, $R^9$ and $R^{10}$ are independently selected from the group consisting of a direct bond and alkylene of 1 to 4 carbons, and $R^{11}$ is alkylene of 2 to 12 carbons.

4. The compound of claim 1 in which the hindered amine light stabilizer group (b) is

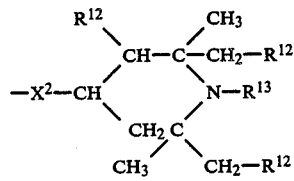

wherein $R^{12}$ is selected from the group consisting of hydrogen and alkyl of 1 to 4 carbons, $R^{13}$ is selected from hydrogen, oxyl, hydroxy, alkyl of 1 to 20 carbons, alkenyl or alkynyl of 3 to 8 carbons, aralkyl of 7 to 12 carbons, aliphatic acyl of 1 to 10 carbons, aromatic acyl of 7 to 13 carbons, alkoxycarbonyl of to 9 carbons, aryloxycarbonyl of 7 to 15 carbons, alkyl, aryl, cycloalkyl substituted carbamoyl of 2 to 13 carbons, aralkyl substituted carbamoyl of 2 2-cyanoethyl, epoxyalkyl of 3 to 10 carbons and polyalkylene oxide of 4 to 30 carbons, $X^2$ is a divalent radical selected from the group consisting of —N(R)—C(=O)—$R^8$—C(=O)—W—, —N(R)—C(=O)—$R^9$—Z—$R^{10}$ — and —N(R)—C(=O)—$R^9$—, R is selected from the group consisting of hydrogen, primary or secondary alkyl of 1 to 8 carbons, aralkyl of 7 to 12 carbons, and cycloalkyl of 5 to 12 carbons, $R^8$ is selected from the group consisting of a direct bond, alkylene of 1 to 14 carbons, oxydialkylene of 4 to 10 carbons, thiodialkylene of 4 to 10 carbons, alkenylene of 2 to 10 carbons, and o-, m-, and p-phenylene, $R^9$ and $R^{10}$ are independently selected from the group consisting of a direct bond and alkylene of 1 to 4 carbons, Z is selected from the group consisting of —N(R)—, —S—, —O— and —N(R)—$R^{11}$—N(R)—, $R^{11}$ is alkylene of 2 to 12 carbons, and W is selected from the group consisting of —Z—, —N(CH$_2$—CH$_2$—C≡N)— and a radical of formula

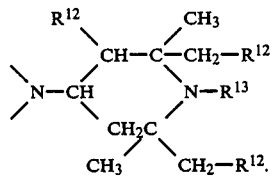

5. The compound of claim 1 in which the dialkyl sulfide group (c) is

—N(R)—C(=O)—$R^{14}$—S—$R^{15}$ wherein

R is selected from the group consisting of hydrogen, primary or secondary alkyl of 1 to 8 carbons, aralkyl of 7 to 12 carbons, and cycloalkyl of 5 to 12 carbons, $R^{14}$ is alkylene of 1 to 4 carbons, and $R^{15}$ is selected from the group consisting of aralkyl of 7 to 12 carbons, alkyl of 1 to 18 carbons and dialkylaminoalkyl of 3 to 12 carbons.

6. The compound of claim 1 in which the hydroxybenzophenone group (d) is

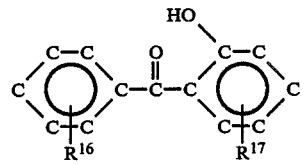

wherein $R^{16}$ and $R^{17}$ are independently selected from the group consisting of hydrogen, hydroxy, alkyl of 1 to 8 carbons, alkoxy of 1 to 8 carbons and a connecting group $X^4$ with the proviso that only one of either $R^{16}$ or $R^{17}$ is the connecting group $X^4$, $X^4$ is a divalent radical selected from the group consisting of —N(R)—C(=O)—$R^9$—Z—, —N(R)—C(=O)—O—$R^9$—Z—, —$R^{26}$—, —N(R)—C(=O)— and —N(R)—S(=O)$_2$—, R is selected from the group consisting of hydrogen, primary or secondary alkyl of 1 to 8 carbons, aralkyl of 7 to 12 carbons, and cycloalkyl of 5 to 12 carbons, $R^9$ and $R^{10}$ are independently selected from the group consisting of a direct bond and alkylene of 1 to 4 carbons, $R^{26}$ is alkylene of 1 to 4 carbons, Z is selected from the group consisting of —N(R)—, —S—, —O— and —N(R)—$R^{11}$—N(R)—, $R^{11}$ is alkylene of 2 to 12 carbons, and the aromatic nuclei have substituents selected from the group consisting of hydroxy, alkyl of 1 to 8 carbons and alkoxy of 1 to 8 carbons.

7. The compound of claim 1 in which the 2-(2-hydroxyphenyl)-2H-benzotriazole group (e) is

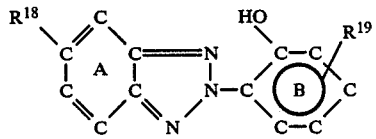

wherein $R^{18}$ is selected from the group consisting of hydrogen, alkyl of 1 to 4 carbons, alkoxy of 1 to 8 carbons, carboxy, alkoxycarbonyl of 2 to 11 carbons, carboxylic acid amide, chlorine, bromine, sulfonic acid, alkylsulfonyl and the connecting group $X^5$, $R^{19}$ is selected from hydrogen, hydroxy, alkyl of 1 to 8 carbons including t-alkyl of 4 to 8 carbons, alkoxy of 1 to 8 carbons, aralkyl of 7 to carbons, aryl of 6 to 14 carbons and the connecting group $X^6$, the substitution being such that only one of the substituents $R^{18}$ and $R^{19}$ is the connecting X⁵ is a divalent radical selected from —N(R)—C(=O)—, —N(R)—S(=O)₂— and X⁶ is selected from the group consisting of a direct bond and a divalent radical selected from the group consisting of —N(R)—C(=O)—R⁸—C(=O)—NH—R⁹—, —N(R)—C(=O)—R⁹—Z—R¹⁰—, —N(R)—C(=O)—O—R⁹, —N(R)—C(=O)—R⁹—, —R¹⁰—, —R²⁶—O—, and —N(R)—C(=O)—, R is selected from the group consisting of hydrogen, primary or secondary alkyl of 1 to 8 carbons, aralkyl of 7 to 12 carbons, and cycloalkyl of 5 to 12 carbons, R⁸ is selected from the group consisting of a direct bond, alkylene of 1 to 14 carbons, oxydialkylene of 4 to 10 carbons, thiodialkylene of 4 to 10 carbons, alkenylene of 2 to 10 carbons, and o-, m-, and p-phenylene, R⁹ and R¹⁰ are independently selected from the group consisting of a direct bond and alkylene of 1 to 4 carbons, R²⁶ is alkylene of 1 to 4 carbons, Z is selected from the group consisting of —N(R)—, —S—, —O— and —N(R)—R¹¹—N(R)—, R¹¹ is alkylene of 2 to 12 carbons, and the aromatic rings A and B have substituents selected from the group consisting of hydrogen, alkyl of 1 to 8 carbons, alkoxy of 1 to 8 carbons, chlorine and bromine.

8. The compound of claim 1 in which the secondary aromatic amine group (f) is

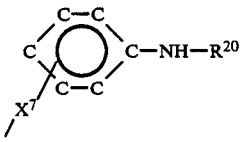

wherein

R²⁰ is selected from the group consisting of aryl of 6 to 14 carbons, alkyl of 1 to 12 carbons and cycloalkyl of 5 to 12 carbons, X⁷ is a divalent radical selected from —N(R)—C(=O)—R⁸—C(=O)—NH— and —N(R)—C(=O)—R⁹—NH—, R is selected from the group consisting of hydrogen, primary or secondary alkyl of 1 to 8 carbons, aralkyl of 7 to 12 carbons, and cycloalkyl of 5 to 12 carbons, R⁸ is selected from the group consisting of a direct bond, alkylene of 1 to 14 carbons, oxydialkylene of 4 to 10 carbons, thiodialkylene of 4 to 10 carbons, alkenylene of 2 to 10 carbons, and o-, m-, and p-phenylene, and R⁹ is selected from the group consisting of a direct bond and alkylene of 1 to 4 carbons.

9. The compound of claim 1 in which the heterocyclic compound (g) is

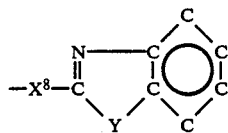

wherein

X⁸ is a divalent radical selected from the group consisting of —N(R)—C(=O)—R⁹—Z— and —N(R)—C(=O)—R⁸—C(=O)—NH—, R is selected from the group consisting of hydrogen, primary or secondary alkyl of 1 to 8 carbons, aralkyl of 7 to 12 carbons, and cycloalkyl of 5 to 12 carbons, R⁸ is selected from the group consisting of a direct bond, alkylene of 1 to 14 carbons, oxydialkylene of 4 to 10 carbons, thiodialkylene of to 10 carbons, alkenylene of 2 to 10 carbons, and o-, m-, and p-phenylene, R⁹ is selected from the group consisting of a direct bond and alkylene of 1 to 4 carbons Z is selected from the group consisting of —N(R)—, —S—, —O— and —N(R)—R¹¹—N(R)—, R¹¹ is alkylene of 2 to 12 carbons, Y is selected from —NH— and —S—, and the aromatic nucleus has substituents selected from the group consisting of hydrogen, hydroxy, alkyl of 1 to 8 carbons, and alkoxy of 1 to 8 carbons.

10. The compound of claim 1 in which the oxanilide derivative (h) is

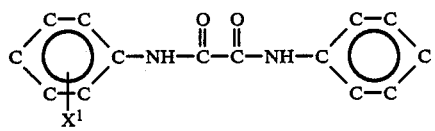

wherein

X¹ is a divalent radical selected from the group consisting of —N(R)—C(=O)—R⁸—C(=O)—NH—, —N(R)—C(=O)—O—R⁹—, —N(R)—C(=O)—R⁹—Z—R¹⁰—, and —N(R)—C(=O)—R⁹—, and

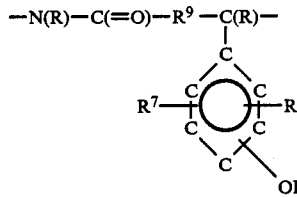

Z is selected from the group consisting of —N(R)—, —S—, —O— and —N(R)—R¹¹—N(R)—, R is selected from the group consisting of hydrogen, primary or secondary alkyl of 1 to 8 carbons, aralkyl of 7 to 12 carbons, and cycloalkyl of 5 to 12 carbons, R⁶ is t-alkyl of 4 to 8 carbons and must be adjacent to the hydroxy substituent, R⁷ is selected from the group consisting of hydrogen, alkyl of 1 to 8 carbons including t-alkyl of 4 to 8 carbons, and alkoxy of 1 to 8 carbons, R⁸ is selected from the group consisting of a direct bond, alkylene of 1 to 14 carbons, oxydialkylene of 4 to 10 carbons, thiodialkylene of to 10 carbons, alkenylene of 2 to 10 carbons, and o-, m-, and p-phenylene, R⁹ and are independently selected from the group consisting of a direct bond and alkylene of 1 to 4 carbons, R¹¹ is alkylene of 2 to 12 carbons, and the aromatic nuclei have substituents selected from the group consisting of hydrogen, alkyl of 1 to 8 carbons, alkoxy of 1 to 4 carbons and halogen.

11. The compound of claim 1 in which the halogen containing amide derivative (i) is

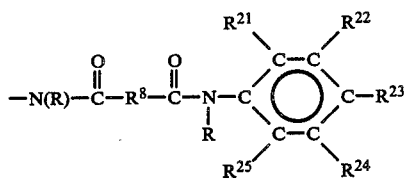

wherein
R is selected from the group consisting of hydrogen, primary or secondary alkyl of 1 to 8 carbons, aralkyl of 7 to 12 carbons, and cycloalkyl of 5 to 12 carbons,
$R^8$ is selected from the group consisting of a direct bond, alkylene of 1 to 14 carbons, oxydialkylene of 4 to 10 carbons, thiodialkylene of 4 to 10 carbons, alkenylene of 2 to 10 carbons, and o-, m-, and p-phenylene,
$R^{21}$, $R^{22}$, $R^{23}$, $R^{24}$, and $R^{25}$ are independently selected from the group consisting of hydrogen, chlorine, bromine, hydroxy, alkoxy or alkylthio of 1 to 12 carbons, acyloxy of 6 to 12 carbons, acylthio of 6 to 12 carbons, aryl of 6 to 12 carbons, alkyl of 1 to 8 carbons, aralkyl of 7 to 13 carbons, and alkoxycarbonyl of 1 to 8 carbons, with the proviso that at least one of $R^{21}$, $R^{22}$, $R^{23}$, $R^{24}$, and $R^{25}$ must be chlorine or bromine.

12. The compound of claim 1 in which A is selected from the group consisting of a linear saturated aliphatic tetravalent radical of 2 to 20 carbons, branched saturated aliphatic tetravalent radical of 2 to 20 carbons, linear unsaturated aliphatic tetravalent radical of 2 to 20 carbons, branched unsaturated aliphatic tetravalent radical of 2 to 20 carbons, saturated alicyclic tetravalent radical of 4 to 12 carbons, unsaturated alicyclic tetravalent radical of 4 to 12 carbons, aralkyl tetravalent radical of 7 to 48 carbons, aralkenyl tetravalent radical of 9 to 48 carbons, aromatic homocyclic tetravalent radical formed of one ring or two or more fused or linked rings each of which contains 5 to 7 carbons, and aromatic heterocyclic tetravalent radical formed of one ring or two or more fused or linked rings each of which contains 4 to 6 carbons and optionally containing heteroatom ring members selected from the group consisting of oxygen, sulfur and nitrogen atoms.

13. The compound of claim 12 wherein A is an aromatic tetravalent radical containing 6 to 24 carbons when aromatic homocyclic, and 4 to 24 carbons having substituents selected from the group consisting of 1 to 6 oxygen, sulfur and nitrogen atoms when heterocyclic, or containing several interlinked cycles, the linking members being selected from the group consisting of a direct bond and a divalent radical selected from —O—, —S—, —SO—, —SO₂—, —CO—, —NR¹—, —COO—, —CHOR¹—, —CF₂—, —N=N—,

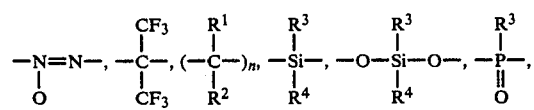

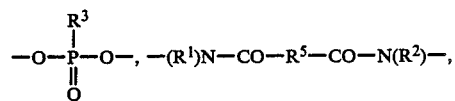

—CO—(R¹)N—R⁵—N(R²)—CO—, —O—CO—R⁵—CO—O—, —CO—O—R⁵—O—CO—, —(R¹)N—CO—N(R²)—, —(R¹)N—COCO—N(R²)—, —CO—N(R¹)— and —O—R⁵—O—, where R¹ and R² are independently selected from the group consisting of hydrogen, alkyl of 1 to 4 carbons, cycloalkyl of 4 to 7 carbons and phenyl,
R³ and R⁴ are independently selected from the group consisting of alkyl of 1 to 4 carbons, cycloalkyl of 4 to 7 carbons and phenyl, and
R⁵ is selected from the group consisting of linear alkylene of 1 to 12 carbons, branched alkylene of 1 to 12 carbons, cycloalkylene of 5 to 12 carbons, arylene of 5 to 20 carbons, diphenylsulfonyl-4,4'-diyl, diphenylsulfonyl-3,4'-diyl, 4,4'-alkylidenediphenyl-1,1'-diyl and 4,3'-alkylidenediphenyl-1,1'-diyl, and
n is an integer of 1–4.

14. The compound of claim 13 wherein substituents for A, R¹, R², R³, R⁴ and R⁵ are selected from the group consisting of alkyl of 1 to 4 carbons, alkoxy of 1 to 4 carbons, acyl of 1 to 4 carbons, acyloxy of 1 to 4 carbons, alkoxycarbonyl of 2 to 5 carbons, arylcarbonyl of 7 to 11 carbons, acryloyloxy, methacryloyloxy, aryloxy of 6 to 10 carbons, aralkyl of 7 to 10 carbons, aryloxycarbonyl of 7 to 11 carbons, phenyl, hydroxy, carboxy, nitrile, chloro, bromo, epoxy, alkylmercapto of 1 to 6 carbons, arylmercapto of 6 to 10 carbons, alkylamino of 1 to 4 carbons, dialkylamino of 2 to 8 carbons, arylamino of 8 carbons, aryl alkylamino of 7 to 10 carbons and trialkoxysilyl of 4 to 9 carbons.

15. The compound of claim 14 in which A is selected from the group consisting of a tetravalent saturated alicyclic radical of 4 to 12 carbons, a tetravalent unsaturated alicyclic radical of 4 to 12 carbons, an aromatic homocyclic radical of one ring or two or more fused or linked rings each of which contains 6 carbons, wherein the linking members are a direct bond or divalent radical selected from the group consisting of —O—, —S—, —SO—, —CO—, —COO—, —CO—O—R⁵—O—CO— or —O—R⁵—O—.

16. The compound of claim 15 in which A is selected from the group consisting of a tetravalent saturated alicyclic radical of 4 to 12 carbons, a tetravalent unsaturated alicyclic radical of 4 to 12 carbons, an aromatic homocyclic radical of one ring or two to six fused or linked rings each of which contains 6 carbons, wherein the linking members are a direct bond or divalent radical selected from the group consisting of —O—, —S—, —CO—, —CO—O—R⁵—O—CO— and —O—R⁵—O—.

17. The compound of claim 16 selected from the group consisting of
N,N'-bis[3-(3,5-di-t-butyl-4-hydroxyphenyl)-propanamido]pyromellitimide,
N,N'-bis[N'-(2,2,6,6-tetramethylpiperidin-4-yl)oxamido]pyromellitimide,
N,N'-bis(3-n-hexylthiopropylamido)pyromellitimide,
N,N'-bis[3-(3,5-di-t-butyl-4-hydroxyphenyl)-propanamido]-3,3',4,4'-benzophenonenetetracarboxylic diimide, N,N'-bis[3-(3,5-di-t-butyl-4-hydroxyphenyl)-
propanamido]-1,4,5,8-naphthalenetetracarboxylic diimide,
2-[2-(2,4,6-tribromophenyl-amino)-2-oxoacetamido]-3a,4,5,7a-tetrahydro-7-methyl-5-[1-(2-[2,4,6-tribromophenylamino]-2-oxoacetamido)-2,5-dioxopyrrollidin-3-yl]-1H-isoindole-1,3(2H)-dione,
N,N'-bis[3-(3,5-di-t-butyl-4-hydroxyphenyl)-
propanamido]-3,3',4,4'-biphenyltetracarboxylic diimide,
4,4'-(4-acetoxy-2,6-dioxa-1,7-dioxoheptane-1,7-diyl)-bis-[N-(3-[3,5-di-t-butyl-4-hydroxyphenyl]-propanamido)phthalimide],
4,4'-(2,5-dioxa-1,6-dioxohexane-1,6-diyl)-bis-[N-(3-[3,5-di-t-butyl-4-hydroxyphenyl]propanamido)phthalimide],
N,N'-bis[N'-(2,4,6-tribromophenyl)oxamido]pyromellitimide,
N,N'-bis[N'-(3,5-di-t-butyl-4-hydroxyphenyl)oxamido]-3,3',4,4'-benzophenonetetracarboxylic diimide, and
N,N'-bis[N'-(3,5-di-t-butyl-4-hydroxyphenyl)oxamido]-pyromellitimide.

18. A polymer composition comprising a synthetic polymer which is subject to thermal, oxidative or actinic light degradation and an effective amount for stabilization of the stabilizer compound of claim 1.

19. The composition of claim 18 wherein the stabilizer compound is added in an amount of about 0.01% to about 10% by weight of the polymer.

20. The composition of claim 18 wherein the stabilizer compound is added in an amount of about 0.05% to about 2% by weight of the polymer.

21. The compound of claim 1 comprising a mixed bis N-(amido)imide stabilizer containing at least two different G groups wherein each G group is selected from any of the monovalent stabilizer radicals (a) through (i).

22. The compound of claim 21 comprising 2-[3-(3,5-di-t-butyl-4-hydroxyphenyl)propanamido]-3a,4,5,7a-tetrahydro-7-methyl-5-[1-(3-hexylthiopropylamido)-2,5-dioxopyrrolidin-3-yl]-1H-isoindole-1,3(2H)-dione.

23. The compound of claim 21 comprising 2-(3-hexylthiopropylamido)-3a,4,5,7a-tetrahydro-7-methyl-5-{1-[3-(3,5-di-t-butyl-4-hydroxyphenyl)propanamido]-2,5-dioxopyrrolidin-3-yl}-1H-isoindole-1,3(2H)-dione.

24. A multifunctional stabilized polymer composition comprising a synthetic polymer which is subject to thermal, oxidative or actinic light degradation and an effective amount for stabilization of more than one stabilizer compound of claim 1.

* * * * *

UNITED STATES PATENT AND TRADEMARK OFFICE
CERTIFICATE OF CORRECTION

PATENT NO. : 4,874,803

DATED : October 17, 1989

INVENTOR(S) : Arthur L. Baron et al.

It is certified that error appears in the above-identified patent and that said Letters Patent is hereby corrected as shown below:

In column 4, line 58, after "to", second occurrence, insert --12--;

line 61, after "to", insert --10--.

In column 7, line 31, change "I2" to --12--.

In column 8, line 41, change "of", first occurrence, to --or--;

line 55, change "2", third occurrence, to --3--; and line 67, insert a hyphen between "3" and "hexylthiopropylamido)pyromellitimide".

In column 11, line 4, insert a space between "and" and "polyimidesulfones"; and

UNITED STATES PATENT AND TRADEMARK OFFICE
CERTIFICATE OF CORRECTION

PATENT NO. : 4,874,803

DATED : October 17, 1989

INVENTOR(S) : Arthur L. Baron et al.

It is certified that error appears in the above-identified patent and that said Letters Patent is hereby corrected as shown below:

line 61, after "stabilizers", insert a semicolon.

In column 20, line 48, insert a hyphen between "7" and "methyl".

In the Claims:

In claim 1, at column 21, amend the formula as follows:

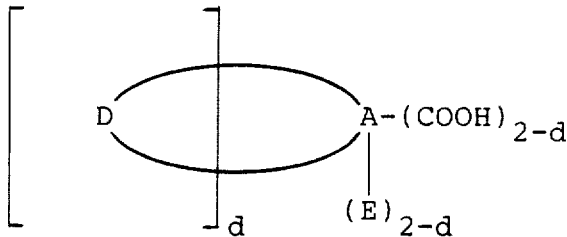

UNITED STATES PATENT AND TRADEMARK OFFICE
CERTIFICATE OF CORRECTION

PATENT NO. : 4,874,803
DATED : October 17, 1989
INVENTOR(S) : Arthur L. Baron et al.

It is certified that error appears in the above-identified patent and that said Letters Patent is hereby corrected as shown below:

In claim 2, at column 22, line 25, change "to", first occurrence, to --of--; and line 61, change "or" to --of--;

at column 23, line 29, change "$-N(CH_2-CH_2)-C\equiv N)-$" to $---N(CH_2-CH_2-C\equiv N)---$;

line 41, change "diakyl" to --dialkyl--; and line 49, change "for" to --from--;

at column 24, line 1, change "6-O-" to --$^{6}$-O---;

at column 25, line 16, insert --the oxanilide-substituted amido group (h) is--;

line 27, insert --the halogenated aromatic-substituted amido group (i) is--; and

UNITED STATES PATENT AND TRADEMARK OFFICE
CERTIFICATE OF CORRECTION

PATENT NO. : 4,874,803

DATED : October 17, 1989

INVENTOR(S) : Arthur L. Baron et al.

It is certified that error appears in the above-identified patent and that said Letters Patent is hereby corrected as shown below:

line 59, before "to", insert --5--; and at column 26, line 25, change "for" to --from--.

In claim 3, at column 27, line 5, before "to", second occurrence, hydroxyalkyl of 1 to 5 carbons, line 31, before "to", insert --2--; and line 33, after "2", first occurrence, insert --to 13 carbons,--;

at column 28, line 31, change "-$R^{26}$-" to ---$R^{10}$-, -$R^{26}$-O---.

Column 27, line 30, after "of" insert --2--

UNITED STATES PATENT AND TRADEMARK OFFICE
CERTIFICATE OF CORRECTION

PATENT NO. : 4,874,803  Page 5 of 6
DATED : October 17, 1989
INVENTOR(S) : Arthur L. Baron et al.

It is certified that error appears in the above-identified patent and that said Letters Patent is hereby corrected as shown below:

In claim 7, at column 28, line 65, before "carbons", second occurrence, insert --12--; and line 68, after "connecting", insert --group, --

In claim 8, at column 30, line 10, after "of", insert --4--.

UNITED STATES PATENT AND TRADEMARK OFFICE
CERTIFICATE OF CORRECTION

PATENT NO. : 4,874,803

DATED : October 17, 1989

INVENTOR(S) : Arthur L. Baron, et al

It is certified that error appears in the above-identified patent and that said Letters Patent is hereby corrected as shown below:

In claim 10, at column 30, line 62, after "of" insert --4--; and line 65, after "and", insert --$R^{10}$--.

Signed and Sealed this

Nineteenth Day of November, 1991

Attest:

HARRY F. MANBECK, JR.

*Attesting Officer*  *Commissioner of Patents and Trademarks*

UNITED STATES PATENT AND TRADEMARK OFFICE
CERTIFICATE OF CORRECTION

PATENT NO. : 4,874,803

DATED : October 17, 1989

INVENTOR(S) : Arthur L. Baron et al.

It is certified that error appears in the above-identified patent and that said Letters Patent is hereby corrected as shown below:

In column 4, line 58, after "to", second occurrence, insert --12--;

line 61, after "to", insert --10--.

In column 7, line 31, change "I2" to --12--.

In column 8, line 41, change "of", first occurrence, to --or--;

line 55, change "2", third occurrence, to --3--; and line 67, insert a hyphen between "3" and "hexylthiopropylamido)pyromellitimide".

In column 11, line 4, insert a space between "and" and "polyimidesulfones"; and

UNITED STATES PATENT AND TRADEMARK OFFICE
CERTIFICATE OF CORRECTION

PATENT NO. : 4,874,803
DATED : October 17, 1989
INVENTOR(S) : Arthur L. Baron et al.

It is certified that error appears in the above-identified patent and that said Letters Patent is hereby corrected as shown below:

line 61, after "stabilizers", insert a semicolon.

In column 20, line 48, insert a hyphen between "7" and "methyl".

In the Claims:

In claim 1, at column 21, amend the formula as follows:

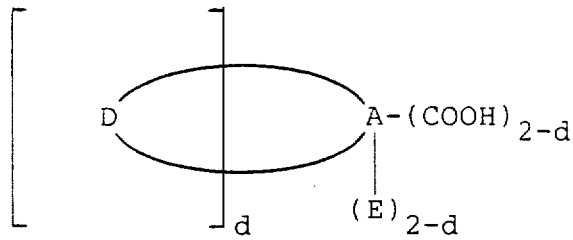

UNITED STATES PATENT AND TRADEMARK OFFICE
CERTIFICATE OF CORRECTION

PATENT NO. : 4,874,803
DATED : October 17, 1989
INVENTOR(S) : Arthur L. Baron et al.

It is certified that error appears in the above-identified patent and that said Letters Patent is hereby corrected as shown below:

In claim 2, at column 22, line 25, change "to", first occurrence, to --of--; and line 61, change "or" to --of--;

at column 23, line 29, change "-N($CH_2$-$CH_2$)-C≡N)-" to ---N($CH_2$-$CH_2$-C≡N)---;

line 41, change "diakyl" to --dialkyl--; and line 49, change "for" to --from--;

at column 24, line 1, change "6-O-" to --$^6$-O---;

at column 25, line 16, insert --the oxanilide-substituted amido group (h) is--;

line 27, insert --the halogenated aromatic-substituted amido group (i) is--; and

UNITED STATES PATENT AND TRADEMARK OFFICE
CERTIFICATE OF CORRECTION

PATENT NO. : 4,874,803

DATED : October 17, 1989

INVENTOR(S) : Arthur L. Baron et al.

It is certified that error appears in the above-identified patent and that said Letters Patent is hereby corrected as shown below:

line 59, before "to", insert --5--; and at column 26, line 25, change "for" to --from--.

In claim 3, at column 27, line 5, before "to", second occurrence, insert --4--;

line 31, before "to", insert --2--; and line 33, after "2", first occurrence, insert --to 13 carbons, hydroxyalkyl of 1 to 5 carbons,--.

at column 28, line 31, change "-$R^{26}$-" to ---$R^{10}$-, -$R^{26}$-O---.

Column 27, line 30, after "of" insert --2--

UNITED STATES PATENT AND TRADEMARK OFFICE
CERTIFICATE OF CORRECTION

PATENT NO. : 4,874,803

DATED : October 17, 1989

INVENTOR(S) : Arthur L. Baron et al.

It is certified that error appears in the above-identified patent and that said Letters Patent is hereby corrected as shown below:

In claim 7, at column 28, line 65, before "carbons", second occurrence, insert --12--; and line 68, after "connecting", insert --group, --

In claim 8, at column 30, line 10, after "of", insert --4--.

UNITED STATES PATENT AND TRADEMARK OFFICE
CERTIFICATE OF CORRECTION

PATENT NO. : 4,874,803

DATED : October 17, 1989

INVENTOR(S) : Arthur L. Baron, et al

It is certified that error appears in the above-identified patent and that said Letters Patent is hereby corrected as shown below:

In claim 10, at column 30, line 62, after "of" insert --4--; and line 65, after "and", insert --$R^{10}$--.

This certificate supersedes Certificate of Correction issued November 19, 1991.

Signed and Sealed this

Twenty-fourth Day of December, 1991

Attest:

HARRY F. MANBECK, JR.

*Attesting Officer*  *Commissioner of Patents and Trademarks*